US008075934B2

(12) United States Patent
Banavara et al.

(10) Patent No.: US 8,075,934 B2
(45) Date of Patent: *Dec. 13, 2011

(54) NUTRITIONAL COMPOSITION WITH IMPROVED DIGESTIBILITY

(75) Inventors: Dattatreya Banavara, Newburgh, IN (US); Win-Chin Chiang, Monroe, NJ (US); Deborah A. Schade, Evansville, IN (US); Joaquin A. Franco, Newburgh, IN (US); Juan M. Gonzalez, Newburgh, IN (US); Dirk Hondmann, Newburgh, IN (US); Zeina E. Jouni, Evansville, IN (US); Yung-Hsiung Lee, Evansville, IN (US); Robert J. McMahon, Evansville, IN (US); Kristin Morris, Evansville, IN (US); Deshanie Rai, Newburgh, IN (US); Gyan P. Rai, Newburgh, IN (US); Nagendra Rangavajla, Dublin, OH (US); Francisco J. Rosales, Newburgh, IN (US); William Michael Russell, Newburgh, IN (US); Eric Van Tol, Arnhem (NL); Hugh N. Tucker, Evansville, IN (US); Donald Carey Walker, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/371,100

(22) Filed: Feb. 13, 2009

(65) Prior Publication Data
US 2010/0104696 A1    Apr. 29, 2010

Related U.S. Application Data

(60) Provisional application No. 61/108,303, filed on Oct. 24, 2008, provisional application No. 61/111,009, filed on Nov. 4, 2008.

(51) Int. Cl.
A23L 1/30    (2006.01)
(52) U.S. Cl. ........................................................ 426/72
(58) Field of Classification Search .................. None
See application file for complete search history.

(56) References Cited

U.S. PATENT DOCUMENTS

| 4,840,814 A | 6/1989 | Harada et al. |
| 4,859,488 A | 8/1989 | Kan et al. |
| 4,906,482 A | 3/1990 | Zemel et al. |

(Continued)

FOREIGN PATENT DOCUMENTS

| CA | 2340103 | 2/2000 |

(Continued)

OTHER PUBLICATIONS

Article by Acta Paediatr Scand., 1985, vol. 74, pp. 45-51 by B. Lundequest, et al. entitled "The Composition of the *Faecal microflora* in Breastfed and Bottle Fed Infants from Birth to Eight Weeks."

(Continued)

*Primary Examiner* — Cherie M Woodward
(74) *Attorney, Agent, or Firm* — Waddey & Patterson, P.C.; James R. Cartiglia

(57) ABSTRACT

The present invention is directed an improved nutritional composition, methods of improving digestion, and methods of enhancing the bioavailability of TGF-β.

23 Claims, 3 Drawing Sheets

U.S. PATENT DOCUMENTS

| | | | |
|---|---|---|---|
| 5,290,571 A | 3/1994 | Bounous et al. | |
| 5,374,567 A | 12/1994 | Cartagena | |
| 5,397,589 A | 3/1995 | Korte et al. | |
| 5,397,591 A | 3/1995 | Kyle et al. | |
| 5,437,880 A | 8/1995 | Takaichi et al. | |
| 5,451,412 A | 9/1995 | Bounous et al. | |
| 5,461,033 A * | 10/1995 | Donnet et al. | 514/5.5 |
| 5,550,156 A | 8/1996 | Kyle | |
| 5,800,830 A | 9/1998 | Asano et al. | |
| 5,840,361 A | 11/1998 | Theuer et al. | |
| 5,866,418 A | 2/1999 | Ballard et al. | |
| 5,942,274 A | 8/1999 | Slattery | |
| 5,952,295 A | 9/1999 | Arnaud-Battandier et al. | |
| 6,057,430 A | 5/2000 | Cerletti | |
| 6,194,208 B1 | 2/2001 | Belford et al. | |
| 6,319,522 B1 | 11/2001 | Ballard et al. | |
| 6,447,808 B2 | 9/2002 | Ballard et al. | |
| 6,576,251 B1 | 6/2003 | Stahl et al. | |
| 6,706,287 B2 | 3/2004 | Ranganathan et al. | |
| 6,733,770 B1 | 5/2004 | Garcia-Rodenas et al. | |
| 6,838,113 B1 | 1/2005 | Buchanen et al. | |
| 6,841,149 B1 | 1/2005 | Spangler et al. | |
| 7,057,016 B2 | 6/2006 | Cerletti | |
| 7,094,550 B2 | 8/2006 | Cerletti | |
| 7,141,262 B2 | 11/2006 | Maubois et al. | |
| 2001/0022980 A1 | 9/2001 | Bell et al. | |
| 2002/0127211 A1 | 9/2002 | Brassart et al. | |
| 2003/0040492 A1 | 2/2003 | Haschke et al. | |
| 2003/0060445 A1 | 3/2003 | Wilson | |
| 2003/0072865 A1 | 4/2003 | Bindels et al. | |
| 2003/0113408 A1 | 6/2003 | Clark et al. | |
| 2003/0129278 A1 | 7/2003 | Stahl et al. | |
| 2003/0157146 A1 | 8/2003 | Rautonen et al. | |
| 2003/0232057 A1 | 12/2003 | Turini et al. | |
| 2004/0062758 A1 | 4/2004 | Mayra-Makinen et al. | |
| 2004/0071824 A1 | 4/2004 | Van Laere et al. | |
| 2004/0072794 A1 | 4/2004 | Kaup et al. | |
| 2004/0077539 A1 | 4/2004 | Maase | |
| 2004/0101597 A1 | 5/2004 | Calapini et al. | |
| 2004/0102377 A1 | 5/2004 | Perrin et al. | |
| 2004/0121042 A1 | 6/2004 | Kudo et al. | |
| 2004/0161422 A1 | 8/2004 | Ranganathan | |
| 2004/0191234 A1 | 9/2004 | Haschke et al. | |
| 2004/0191295 A1 | 9/2004 | Locniskar et al. | |
| 2004/0219157 A1 | 11/2004 | Rochat et al. | |
| 2005/0158425 A1 | 7/2005 | Bouman et al. | |
| 2005/0250697 A1 | 11/2005 | Maubois et al. | |
| 2005/0271641 A1 * | 12/2005 | Bjorksten et al. | 424/93.45 |
| 2006/0233915 A1 * | 10/2006 | Puski et al. | 426/72 |
| 2006/0240148 A1 | 10/2006 | Nguyen et al. | |
| 2006/0286210 A1 * | 12/2006 | Rangavajla et al. | 426/72 |
| 2007/0207132 A1 | 9/2007 | Speelmans et al. | |
| 2008/0095752 A1 | 4/2008 | Chiang et al. | |

FOREIGN PATENT DOCUMENTS

| | | |
|---|---|---|
| EP | 0313515 | 3/1992 |
| EP | 0339656 | 11/1994 |
| EP | 0374390 | 6/1995 |
| EP | 0527283 | 11/1997 |
| EP | 0852913 | 7/1998 |
| EP | 0759029 | 7/1999 |
| EP | 1034704 | 9/2000 |
| EP | 1161152 | 10/2004 |
| EP | 0545946 | 1/2005 |
| EP | 1218410 | 6/2005 |
| EP | 1345624 | 6/2006 |
| EP | 1779863 | 5/2007 |
| WO | 9200994 | 1/1992 |
| WO | 0054603 | 9/2000 |
| WO | 0125276 | 4/2001 |
| WO | 02051437 | 7/2002 |
| WO | 02083164 | 10/2002 |
| WO | 2005039318 | 5/2005 |
| WO | 2005039319 | 5/2005 |
| WO | 2005039597 | 5/2005 |

OTHER PUBLICATIONS

Article by BMJ, 1999, vol. 318, pp. 999-1003 by George T. Macfarlane et al. entitled "Probiotics and prebiotics: can regulating the activities of intestinal bacteria benefit health?"

A review published in Geneva 1994 by Gordon & Breach Science, pp. 90-106, Chapter 5 by Keisuke Matsumoto et al. entitled "Galactooligosaccharides."

Article by Child: Care, Health and Development, 1997, vol. 23, No. 6, pp. 475-478 by R. Morley et al. entitled Infant Feeding and maternal concerns about stool harness.

Article by Acta Paediatr, 2003, Suppl. 441, pp. 77-79 by GE Moro, et al. entitled "Effects of a new mixture of prebiotics on *Faecal flora* and stools in term infants."

Article by Acta Paediatrica, 2005, vol. 94, Suppl. 449, pp. 27-30 by Guido Moro et al. entitled Dietary prebiotic oligosaccharides are detectable in the faeces of formula-fed infants.

Article by Acta Paediatr, 1999, Suppl. 430, pp. 47-57 by K. Orrhage et al. entitled "Factors controlling the bacterial colonization of the intestine in breastfed infants."

Article by Journal of Pediatric Gastroenterology and Nutrition, 1995, vol. 20, pp. 81-90 by P.T. Quinlan et al. entitled "The Relationship between Stool Hardness and Stool Composition in Breast and Formula-Fed Infants."

Article from Immunology and Medical Microbiology, 2005, vol. 43, pp. 59-65 by Minna M. Rinne et al. entitled "Similar bifidogenic effects of prebiotic-supplemented partially hydrolyzed infant formula and breastfeeding on infant gut microbiota."

Article by Eur J. Nutr, 2002, vol. 41, pp. 85-92 by Silvia Rudloff et al. entitled "Detection of ligands for selectins in the oligosaccharide fraction of human milk."

Article by Am J Clin Nutr, 2001, vol. 73 (Suppl.), pp. 459S-464S by Katharina E. Scholz-Ahrens et al. entitled "Effects of prebiotics on mineral metabolism."

Abstract from PubMed by Indian J. Matern Child Health, 1993, vol. 4, No. 2, pp. 62-63 by K. Singh et al. entitled "Mothers' concept of the ideal number, colour and consistency of stools of their infants." Online at www.ncbi.nlm.nig.gov/entrez/query.fcgi?CMD=search&DB=pubmed.

Article by British Journal of Nutrition, 1999, vol. 81, pp. 121-132 by Jan Van Loo et al. entitled "Functional food properties of non-digestible oligosaccharides: a consensus report from the ENDO project (DGXII AIRII-CT94-1095)."

Article from J Nutr, 1979, vol. 109, pp. 1682-1687 by Fred H. Mattson et al. entitled "The absorbability by Rats of Various Triglycerides of Stearic and Oleic Acid and the Effect of Dietary Calcium and Magnesium." Online at jn.nutrition.org/cgi/content/abstract/109/10/1682.

Article online by Dairy Foods Magazine, Oct. 2003 by Donna Brooks entitled "Polydextrose For Adding Fiber." Online at www.dairyfoods.com.

Article by Chinese Medical Journal, 2004, vol. 117 No. 6, pp. 927-931 by X. Ben et al. entitled "Supplementation of milk formula with galacto-oligosaccharides improves intestinal micro-flora and fermentation in term infants." Online at www.cmj.org/information/full.asp?id=1655.

Article by Current Pharmaceutical Design, 2005, vol. 11, pp. 55-74 by M.J. Kullen et al. entitled "The Delivery of Probiotics and Prebiotics to Infants."

Article by Early Human Development, 2001, vol. 65 Suppl., pp. 43-52 by M. Rivero-Urgell et al. entitled "Olgiosaccharides: application in infant food."

Article by American Journal Clinical Nutrition, 2001, vol. 73 Suppl., pp. 444-450 by E. Isolauri et al. entitled "Probiotics: effects on immunity1-3."

Article by American Journal Clinical Nutrition, 2001, vol. 73 Suppl., pp. 415-420 by J. Cummings et al. entitled "Prebiotics digestion and fermentation1-3."

Article by American Society for Nutritional Sciences, Nutritional Immunology-Research Communication, 2003, pp. 153-156, by M. Roller et al. entitled "Prebiotic Inulin Enriched with Oligofructose in Combination with the Probiotic *Lactobacillus rhamnosus* and *Bifidobacterium lactis* Modulates Intestinal Immune Functions in Rats1."

Article from Journal of Medicinal Food, 2005, vol. 8(1), pp. 113-116 by Pylkans et al. entitled "Comparison of Different Fibers for In Vitro Production of short Chain Fatty Acids by Intestinal Microflora."

Article by Applied and Environmental Microbiology, Aug. 2004, vol. 70, No. 8, pp. 4505-4511 by H. Probert et al. entitled "Polydextros, Lactitol, and Fructo-Oligosaccharide Fermentation by Colonic Bacteria in a Three-Stage Continuous Culture System."

Article from Journal of Family Practice, Aug. 2002 by Mark R. Ellis entitled "What is the best therapy for constipation in infants?"—Clinical inquiries: from the Family Practice Inquiries Network. Online at www.findarticles.com/p/articles/mi_m0689/is_8_51/ai_90464039/print.

Article from Chinese Medical Journal, 2004, vol. 117 No. 6, pp. 927-931 by Ben Xiao-ming, et al. entitled Supplementation of milk formula with galacto-oligosaccharides improves intestinal microflora and fermentation in term infants. Online at http://www.Cmj.org/Periodical/PaperList.asp?id=LW8945.

Article from Am J Clin Nutr, 2000, vol. 72 pp. 1503-1509 by Zhong Jie, et al. entitled Studies on the effects of polydextrose intake on physiologic functions in Chinese people1-3.

Article from Journal of Pediatric Gastroenterology and Nutrition, May 2001, vol. 32, pp. 534-541 by Tianan Jiang et al. entitled "Gas Production by Feces of Infants."

Article from Journal of Pediatric Gastroenterology and Nutrition, Nov. 2004, vol. 39, pp. 465-473 by Carlo Agostoni, et al. entitled "Prebiotic Oligosaccharides in Dietetic Products for Infants: A Commentary" by the ESPGHAN Committee on Nutrition.

Article by Nutrition, 2002, vol. 18, pp. 484-489 by Pedro A. Alarcon et al. entitled "Gastrointestinal Tolerance of a New Infant Milk Formula in Healthy Babies: An International Study Conducted in 17 Countries."

Article from J. Clin Gastroenteroal, Jul. 2004, vol. 38, Supp. 2 pp. S76-S79 by G. Boehm et al. entitled "Prebiotic in Infant Formulas."

Article from Acta Paediatrica, 2005, vol. 94 (Suppl. 449), pp. 18-21 by Gunther Boehm et al. entitled "Prebiotic Carbohydrates in Human Milk and Formulas."

Article from Arch. Dis. Child. Fetal Neonatal Ed., 2002, vol. 86, pp. F178-F181 by G. Boehm et al. entitled Supplementation of a bovine milk formula with an oligosaccharide mixture increases counts of faecal bifidobacteria in preterm infants. Online at http://www.bmjjournals.com.

ESPGHAN Abstracts by J. Pediatr Gastroenterology Nutr., Apr. 2003, vol. 36(4), No. P179 by G. Boehm et al. entitled Effect of increasing number of intestinal bifidobacteria on the presence of clinically relevant pathogens.

Article from Pediatrics, May 1993, vol. 91, No. 5, pp. 908-914 by Christi K. Bradley et al. entitled "Evaluation of Two Iron-Fortified, Milk-Based Formulas During Infancy."

Article from Pediatric Research, 2006, vol. 59, No. 3, pp. 451-456 by Oscar Brunser et al. entitled "Effect of Milk Formula with Prebiotics on the Intestinal Microbiota of Infants After an Antibiotic Treatment."

Article from Journal of Pediatric Gastroenterology and Nutrition, 2000, vol. 30, pp. 181-192 by Renee M. Erney et al. entitled "Variability of Human Milk Neutral Oligosaccharides in a Diverse Population."

Article from Acta Paediatr, 2003, Supp. 441, pp. 48-55 by S. Fanaro et al. entitled "Intestinal Microflora in Early Infancy: Composition and Development."

Article from Journal of Pediatric Gastroenterology and Nutrition, Aug. 2005, vol. 41, pp. 186-190 by S. Fanaro et al. entitled "Acidic Oligosaccharides from Pectin Hydrolysate as New Component for Infant Formulai: Effect on Intestinal Flora, Stool Characteristics, and pH."

Article from J. Nutr., 1999, vol. 129, pp. 1438S-1441S by Glenn R. Gibson entitled "Dietary Modulation of the Human Gut Microflora Using the Prebiotics Oligofructose and Inulin."

Article from J. Nutr., 1995, vol. 125, pp. 1401-1412 by Glenn R. Gibson et al. entitled "Dietary Modulation of the Human Colonic Microbiota: Introducing the Concept of Prebiotics."

Article from Pediatrics, 1995, vol. 95, pp. 50-54 by Jeffrey S. Hyam et al. entitled "Effect of Infant Formula on Stool Characteristics of Young Infants."

Article from Journal of Pediatric Gastroenterology and Nutrition, Mar. 2003, vol. 36, pp. 301-310 by Lawrence T. Weaver entitled "Improving Infant Milk Formulas: Near the End of the Trail for the Holy Grail?"

Article from Microbiol. Immunol., 1984, vol. 28, No. 9, pp. 975-986 by Yoshimi Benno et al. entitled "The Intestinal Microflora of Infants: Composition of Fecal Flora in Breast-Fed and Bottle-Fed Infants."

ESPGHAN Abstracts from Journal of Pediatric Gastroenterology and Nutrition, Apr. 2002, vol. 34(4), p. 477, No. 2 by Knol et al. entitled "Bifidobacterial species that are present in breast fed infants are stimulated in formula fed infants by changing to a formula containing prebiotics."

Article from Lipids, 1991, vol. 26, pp. 250-253 by R.J. Jandacek entitled "The Solubilization of Calcium Soaps by Fatty Acids."

Article from Journal Clinical Microbiology, Feb. 1987, pp. 285-289 by Elisabeth A.E. Mevisen, et al. entitled "*Bifidobacterium, Bacteroides,* and *Clostridium* spp. In Fecal Samples from Breast-Fed and Bottle-Fed Infants with and without Iron Supplement."

A book entitled Handbook of Milk Composition (1995) published by Academic Press, San Diego, Chapter 4, pp. 273-349, by David S. Newburg et al. entitled "Carbohydrates in Milks Analysis, Quantities and Significance."

Article by the EFSA Journal, 2004, vol. 31, pp. 1-11 entitled "Opinion of the Scientific Panel on Dietetic Products, Nutrition and Allergies on a request from the Commission relating to the safety and suitability for particular nutritional use by infants of fructooligosaccharides in infant formulae and follow-on formulae."

Article by Am J Clin Nutr, 1999, vol. 70, pp. 920-927 by Kathy Kennedy et al. entitled "Double-blind, randomized trial of a synthetic triacylglycerol in formula-fed term infants: effects on stool biochemistry, stool characteristics, and bone mineralization1-3."

ESPR Abstracts from J. Pediatr Gastroenterol Nutr., 2005, p. 487, Abstract No. 134 by C. van Limpt et al. entitled "Effect of Colonic Short Chain Fatty Acids, Lactate and pH on the Growth of Common Gut Pathogens."

Article by Pediatrics, Jan. 1999, vol. 103, No. 1, pp. 1-6 by Beate Lloyd et al. entitled "Formula Tolerance in Postbreastfed and Exclusively Formula-fed Infants."

Craig, S.A.S., et al., Polydextrose as Soluble Fiber: Physiological and Analytical Aspects, Cereal Foods World, vol. 43, No. 5, p. 370-376, May 1998.

Moro, G., et al., Dosage-Related Bifidogenic Effects of Galacto- and Fructooligosaccharides in Formula-Fed Term Infants, J. Pediatr Gastroenterol Nutr, vol. 34, No. 3, Mar. 2002.

Roberfroid, M.B., Health benefits of non-digestible oligosaccharides, Adv Exp Med Biol. 1997;427:211-9. Review. PubMed PMID: 9361846. Abstract only.

"Lactulose" pp. 1-5, Retrieved from www.gettingwell.com/drug_info/nmdrugprofiles/nutsuppdrugs/lac_0300.shtml (Feb. 1, 2005).

* cited by examiner

NUTRITIONAL COMPOSITION WITH IMPROVED DIGESTIBILITY

CROSS-REFERENCES TO RELATED APPLICATIONS

This application claims benefit of the following patent application(s) which is/are hereby incorporated by reference: U.S. Provisional Application Ser. No. 61/108,303 filed Oct. 24, 2008 and U.S. Provisional Application Ser. No. 61/111,009 filed Nov. 4, 2008.

BACKGROUND OF THE INVENTION

Field of the Invention

The present invention relates generally to the field of nutritional compositions.

SUMMARY OF THE INVENTION

Briefly, the present invention is directed, in an embodiment, to a nutritional composition comprising a protein source, a carbohydrate source, a fat source, a supplemental calcium source, DHA, ARA, a prebiotic, and TGF-β. In some embodiments, the calcium source may be calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof. In certain embodiments, the prebiotic may be galacto-oligosaccharide or a combination of galacto-oligosaccharide and polydextrose.

The invention is also directed, in a particular embodiment, to a nutritional product comprising a protein source comprising about 1.8 to about 2.5 g/100 Kcal; a fat source comprising about 5.5 to about 5.7 g/100 Kcal; a carbohydrate source comprising about 10.5 to about 11.0 g/100 Kcal; a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof; DHA comprising about 15 to about 20 mg/100 Kcal; ARA comprising about 23 to about 27 mg/100 Kcal; a prebiotic comprising about 0.5 to about 0.7 mg/100 Kcal galacto-oligosaccharide or about 0.2 to about 0.4 mg/100 Kcal polydextrose and about 0.2 to about 0.4 mg/100 Kcal galacto-oligosaccharide; and transforming growth factor (TGF)-β.

The invention is also directed to a nutritional product comprising a protein source comprising about 1.8 to about 2.5 g/100 Kcal; a fat source comprising about 5.5 to about 5.7 g/100 Kcal; a carbohydrate source comprising about 10.5 to about 11.0 g/100 Kcal; a supplemental calcium source selected from the group consisting of calcium gluconate, calcium D-saccharate, calcium aspartate, calcium propionate, and combinations thereof; DHA comprising about 15 to about 20 mg/100 Kcal; ARA comprising about 23 to about 27 mg/100 Kcal; a prebiotic comprising about 0.5 to about 0.7 mg/100 Kcal galacto-oligosaccharide; or about 0.2 to about 0.4 mg/100 Kcal polydextrose and about 0.2 to about 0.4 mg/100 Kcal galacto-oligosaccharide; and TGF-β.

The present invention is additionally directed, in an embodiment, to a nutritional product comprising a protein source comprising about 1.8 to about 2.5 g/100 Kcal; a fat source comprising about 5.5 to about 5.7 g/100 Kcal; a carbohydrate source comprising about 10.5 to about 11.0 g/100 Kcal; calcium gluconate as the sole supplemental calcium source; DHA comprising about 15 to about 20 mg/100 Kcal; ARA comprising about 23 to about 27 mg/100 Kcal; a prebiotic comprising about 0.5 to about 0.7 mg/100 Kcal galacto-oligosaccharide or about 0.2 to about 0.4 mg/100 Kcal polydextrose and about 0.2 to about 0.4 mg/100 Kcal galacto-oligosaccharide; and TGF-β.

Additionally, the invention is directed, in an embodiment, to a nutritional product comprising a protein source comprising about 1.8 to about 2.5 g/100 Kcal; a fat source comprising about 5.5 to about 5.7 g/100 Kcal; a carbohydrate source comprising about 10.5 to about 11.0 g/100 Kcal; a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof; DHA comprising about 15 to about 20 mg/100 Kcal; ARA comprising about 23 to about 27 mg/100 Kcal; a prebiotic comprising about 0.2 to about 0.4 mg/100 Kcal polydextrose and about 0.2 to about 0.4 mg/100 Kcal galacto-oligosaccharide; and TGF-β.

In some embodiments, the invention is directed to a method for making a nutritional composition which forms softer curds upon acidification in the human gut, the method comprising combining a protein source, a carbohydrate source, a fat source, and a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof.

In other embodiments, the invention is directed to a method for making a nutritional composition which forms smaller curds upon acidification in the human gut, the method comprising combining a protein source, a carbohydrate source, a fat source, and a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof.

In yet another embodiment, the invention is directed to a method for making a nutritional composition having improved digestibility, the method comprising combining a protein source, a carbohydrate source, a fat source, and a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof.

Further, the invention is directed, in an embodiment, to a method for enhancing the bioavailability of calcium in a nutritional composition, the method comprising combining a protein source, a carbohydrate source, a fat source, and a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof.

Finally, the invention is directed, in an embodiment, to a method for making a nutritional composition having enhanced TGF-β bioactivity, the method comprising combining a protein source, a carbohydrate source, a fat source, and a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof.

BRIEF DESCRIPTION OF THE DRAWINGS

A full and enabling disclosure of the present invention, including the best mode thereof directed to one of ordinary skill in the art, is set forth in the specification, which refers to the appended figures, in which.

DETAILED DESCRIPTION OF THE PREFERRED EMBODIMENTS

Figure 1:
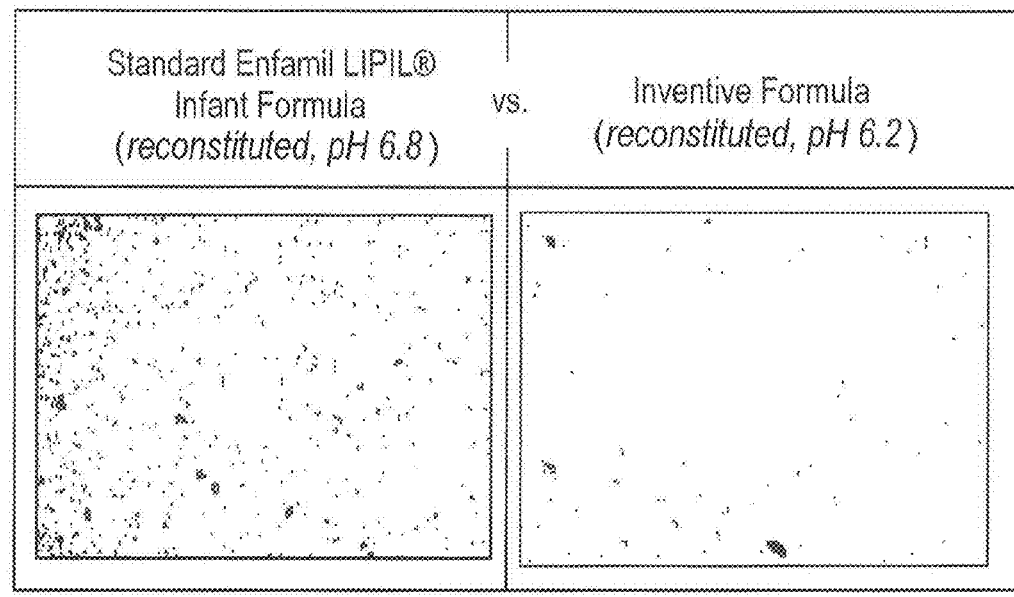
FIG. 1 illustrates a comparison of standard formula versus the inventive formula with regard to curd formation.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As set forth above, the present invention relates generally to nutritional compositions having improved digestibility. References related to such compositions may include U.S. Pat. No. 6,838,113 to Buchanen, et al. or U.S. Pat. No. 5,942,274 to Slattery.

The technical problem to be solved by the present invention is to provide novel nutritional products that are easily digested, provide physiochemical benefits, and/or provide physiological benefits. In an embodiment of the present invention, the inventors have discovered a nutritional composition comprising a protein source, a fat source, a carbohydrate source, a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof, DHA, ARA, a prebiotic comprising galacto-oligosaccharide or polydextrose and galacto-oligosaccharide, and TGF-β.

The term "supplemental calcium source," as used herein, means a calcium source, in the form of a salt, which is added to the nutritional composition. The term does not include calcium which is inherent in other components of the nutritional product.

In a particular embodiment, the nutritional product comprises:
  a. a protein source comprising about 2.0 to about 2.2 g/100 Kcal;
  b. a fat source comprising about 5.5 to about 5.7 g/100 Kcal;
  c. a carbohydrate source comprising about 10.5 to about 11.0 g/100 Kcal;
  d. a supplemental calcium source comprising calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof;
  e. DHA comprising about 15 to about 20 mg/100 Kcal;
  f. ARA comprising about 23 to about 27 mg/100 Kcal;
  g. a prebiotic comprising:
    i. about 0.5 to about 0.7 mg/100 Kcal galacto-oligosaccharide; or
    ii. about 0.2 to about 0.4 mg/100 Kcal polydextrose and about 0.2 to about 0.4 mg/100 Kcal galacto-oligosaccharide; and
  h. TGF-β.

In some embodiments, the nutritional product may be an infant formula. As used herein, the term "infant" means a person not more than 12 months of age. The term "infant formula" applies to a composition in liquid or powdered form intended for use, where necessary, as a substitute for human milk (breast milk substitute) in meeting the normal nutritional requirements of infants. In a separate embodiment, the nutritional product may be a human milk fortifier, meaning it is a composition which is added to human milk in order to enhance the nutritional value of human milk. As a human milk fortifier, the inventive composition may be in powder or liquid form. In another embodiment, the inventive nutritional product may be a follow-up formula. The term "follow-up formula" as used herein refers to foods intended for use as a liquid part of the weaning diet for the infant from the 6$^{th}$ month of life on and for young children. As used herein, the term "young child" or "young children" means persons from the age of more than 12 months up to the age of three years. In yet another embodiment, the inventive nutritional product may be a children's nutritional composition. The term "child" or "children" as used herein means persons over the age of 3 years and prior to adolescence. In still another embodiment, the inventive nutritional product may be a growing-up milk. The term "growing-up milk" refers to a broad category of milk-based fortified beverages intended to be used as a part of a diverse diet in order to support the normal growth and development of children from the ages of 1 to 6 years.

In some embodiments, the composition is an acidified product. As used herein, the term "acidified product" refers to a nutritional composition which has a finished equilibrium pH of 4.6 or below and a water activity greater than 0.85. In still another embodiment, the nutritional product may be a medical food. The term "medical food" is defined as a food which is formulated to be consumed or administered enterally under the supervision of a physician and which is intended for the specific dietary management of a disease or condition for which distinctive nutritional requirements, based on recognized scientific principles, are established by medical evaluation. In general, to be considered a medical food, a product must, at a minimum, meet the following criteria: the product must be a food for oral or tube feeding; the product must be labeled for the dietary management of a specific medical disorder, disease or condition for which there are distinctive nutritional requirements; and the product must be intended to be used under medical supervision.

The nutritional products of the invention may provide minimal, partial, or total nutritional support. The compositions may be nutritional supplements or meal replacements. In some embodiments, the compositions may be administered in conjunction with a food or nutritional composition. In this embodiment, the compositions can either be intermixed with the food or other nutritional compositions prior to ingestion by the subject or can be administered to the subject either before or after ingestion of a food or nutritional composition. The compositions may be administered to preterm infants receiving infant formula, breast milk, a human milk fortifier, or combinations thereof.

The compositions may, but need not, be nutritionally complete. The skilled artisan will recognize "nutritionally complete" to vary depending on a number of factors including, but not limited to, age, clinical condition, and dietary intake of the subject to whom the term is being applied. In general, "nutritionally complete" means that the nutritional composition of the present invention provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The composition which is "nutritionally complete" for the preterm infant will, by definition, provide qualitatively and quantitatively adequate amounts of all carbohydrates, lipids, essential fatty acids, proteins, essential amino acids, conditionally essential amino acids, vitamins, minerals, and energy required for growth of the preterm infant. The composition which is "nutritionally complete" for the term infant will, by definition, provide qualitatively and quantitatively adequate amounts of all carbohydrates, lipids, essential fatty acids, proteins, essential amino acids, conditionally essential amino acids, vitamins, minerals, and energy required for growth of the term infant. The composition which is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

The nutritional composition may be provided in any form known in the art, including a powder, a gel, a suspension, a paste, a solid, a liquid, a liquid concentrate, or a ready-to-use product.

If the nutritional product is an infant formula or human milk supplement, it may be a product for a full-term infant, a preterm infant, a low-birth-weight infant, a very-low-birth-weight infant, or an extremely low birth weight infant. As used herein, the term "full-term" refers to neonatal infants born after about 37 weeks of gestation through 42 weeks gestation but less than 1 month of age. The term "full-term infant" or "infant" as used herein refers to an infant less than twelve months of age. As used herein, the terms "preterm" or "preterm infant" includes infants born prior to about 37 weeks of gestation. As used herein, the term "low birth weight" or "low birth weight infant" are those infants are those weighing from about 3.3 to about 5.5 pounds at birth. "Very-low-birth-weight infants" are those weighing less than about 3.3 to about 2.2 pounds at birth. "Extremely low birth weight" or "extremely low birth weight infants" are those weighing less than 2.2 pounds at birth.

In certain embodiments, the nutritional product formed via the method of the invention may be administered enterally or parenterally. As used herein, "enteral" means through or within the gastrointestinal, or digestive, tract, and "enteral administration" includes oral feeding, intragastric feeding, transpyloric administration, or any other introduction into the digestive tract. The term "parenterally" means taken into the body or administered in a manner other than through the digestive tract, such as by intravenous or intramuscular injection.

In an embodiment, the amount of lipid or fat in the composition may vary from about 4 to about 7 g/100 kcal. In another embodiment, the amount of fat may vary from about 5 to about 6 g/100 kcal. In a further embodiment, the amount of fat may vary from about 5.3 to about 5.6 g/100 kcal. In yet another embodiment, the amount of fat may vary from about 5.4 to about 5.9 g/100 kcal. In still another embodiment, the amount of fat may vary from about 5.5 to about 5.7 g/100 kcal. Suitable lipid sources for practicing the present invention may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In an embodiment of the invention, the amount of protein in the composition may vary from about 1 to about 5 g/100 kcal. In another embodiment, the amount of protein may be from about 1.8 to about 2.5 g/100 kcal. In another embodiment, the amount of protein may be from about 2.0 to about 2.2 g/100 kcal. In one embodiment, the amount of protein may be about 2.1 g/100 kcal. Bovine milk protein sources useful in practicing the present invention include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In an embodiment of the invention, the proteins are provided as intact proteins. In other embodiments, the proteins are provided as a combination of both intact proteins and partially hydrolyzed proteins, with a degree of hydrolysis of between about 4% and 10%. In yet another embodiment, the protein source may be supplemented with glutamine-containing peptides.

In a particular embodiment of the invention, the whey: casein ratio is similar to that found in human breast milk. In an embodiment, the protein source comprises from about 40% to about 70% whey protein. In another embodiment, the protein source may comprise from about 30% to about 60% caseins. In one embodiment, the protein source may comprise from about 40% to about 70% whey protein and from about 30% to about 60% caseins.

The amount of carbohydrate in the composition of the invention may, in an embodiment, vary from about 8 to about 12 g/100 kcal. In another embodiment, the amount of carbohydrate may vary from about 10.5 to 11 g/100 kcal. In a particular embodiment, the amount of carbohydrate may be about 10.6 g/100 kcal. Carbohydrate sources may be any known or used in the art, e.g., lactose, fructose, glucose, corn syrup, corn syrup solids, maltodextrins, sucrose, starch, rice syrup solids, rice starch, modified corn starch, modified tapioca starch, rice flour, soy flour, and combinations thereof.

In a particular embodiment, the carbohydrate component may be comprised of 100% lactose. In yet another embodiment, the carbohydrate component comprises between about 0% and 60% lactose. In another embodiment, the carbohydrate component comprises between about 15% and 55% lactose. In yet another embodiment, the carbohydrate component comprises between 20% and 30% lactose. In these embodiments, the remaining source of carbohydrate may be provided by one or more of those known in the art including, but not limited to those previously disclosed as suitable for practicing the present invention.

The nutritional composition of the present invention may optionally include one or more of the following vitamins or derivatives thereof, including, but not limited to, biotin, biotin trituration, vitamin $B_1$ (e.g., thiamin, thiamin pyrophosphate, thiamin hydrochloride, thiamin triphosphate, thiamin mononitrate), vitamin $B_2$ (e.g., riboflavin, flavin mononucleotide, flavin adenine dinucleotide, lactoflavin, ovoflavin, sodium riboflavin, riboflavin-5'-phosphate), vitamin $B_3$ (e.g., niacin, nicotinic acid, nicotinamide, niacinamide, nicotinamide adenine dinucleotide, nicotinamide mononucleotide, nicotinamide adenine dinucleotide phosphate, pyridine-3-carboxylic acid, vitamin $B_3$ precursor tryptophan), folic acid (e.g., folate, folacin, pteroylglutamic acid, pteroylmonoglutamic acid, pteroylpolyglutamates), pantothenic acid (e.g., pantothenate, panthenol, calcium pantothenate), vitamin $B_6$ (e.g., pyridoxine hydrochloride, pyridoxine, pyridoxine-5'-phosphate, pyridoxal, pyridoxal-5'phosphate, pyridoxamine, pyridoxamine-5'-phosphate, pyridoxine glucoside), vitamin $B_{12}$ (e.g., cobalamin, methylcobalamin, deoxyadenosylcobalamin, cyanocobalamin, hydroxycobalamin, adenosylcobalamin, 5'-deoxyadenosylcobalamin), vitamin C (e.g., ascorbic acid, dehydroascorbic acid, L-ascorbic acid, sodium L-ascorbate, calcium L-ascorbate, ascorbyl palmitate), vitamin A (e.g., retinol, retinal, retinoic acid, vitamin A palimitate, retinyl acetate, retinyl palmitate, retinyl palmitate esters, retinyl esters, retinol esters), β-carotene, α-carotene, vitamin D (e.g., vitamin $D_3$, calciferol, cholecalciferol, dihydroxyvitamin D, 1,25-dihydroxycholecalciferol, 7-dehyrdocholesterol, ergocalciferol), choline (e.g., choline chloride, choline bitartrate, lysophosphatidylcholine), vitamin E (e.g., vitamin E acetate, vitamin E tocopheryl acetate, α-tocopherol, α-tocopherol acetate, α-tocopherol succinate, α-tocopherol nicotinate, α-tocopherol esters, RRR-α-tocopherol, RRR-α-tocopherol acetate, RRR-α-tocopherol succinate, dL-α-tocopheryl acetate, dL-α-tocopheryl succinate, dL-α-tocopherol, dL-α-tocopherol acetate, dL-α-tocopherol succinate, γ-tocopherol), vitamin K (e.g., vitamin $K_1$ phytonadione, vitamin $K_2$, vitamin $K_3$, menadione, menaquinone, menaquinone-7, menaquinone-4, menaquinone-8, menaquinone-8H, menaquinone-9, menaquinone-9H, menaquinone-10, menaquinone-11, menaquinone-12, menaquinone-13, phylloquinone, naphthoquinone, 2',3'-dihydrophylloquinone), carnitine, L-carnitine, inositol, taurine, and any combinations thereof.

The nutritional composition of the present invention may optionally include one or more of the following minerals or derivatives thereof, including, but not limited to, boron, calcium, calcium acetate, calcium aspartate, calcium carbonate, calcium chloride, calcium citrate, calcium citrate malate, calcium D-saccharate, calcium gluconate, calcium gluconate monohydrate, calcium glycerol phosphate, calcium lactate, calcium phosphate, calcium propionate, calcium sulfate, chloride, chromium, chromium chloride, chromium picolinate, trivalent chromium, copper, copper gluconate, cupric sulfate, fluoride, iodide, iodine, calcium iodate, cuprous iodide, potassium iodate, potassium iodide, iron, iron trituration, elemental iron, ferrous sulfate heptahydrate, carbonyl iron, ferric iron, ferrous gluconate, ferrous glycine sulfonate, ferrous iron, ferrous fumarate, ferric orthophosphate, polysaccharide iron, magnesium, magnesium carbonate, magnesium hydroxide, magnesium oxide, magnesium phosphate, magnesium stearate, magnesium sulfate, manganese, manganese acetate, manganese chloride, manganese sulfate monohydrate, molybdenum, sodium molybdate, anhydrous molybdenum, phosphorus, potassium, potassium acetate, potassium bicarbonate, potassium chloride, potassium citrate, potassium hydroxide, potassium phosphate, selenium, selenate, selenite trituration, sodium docusate, sulfur, sodium, sodium chloride, sodium citrate, sodium selenite, sodium sulfate, inorganic sulfate, zinc, zinc gluconate, zinc oxide, zinc sulfate, zinc sulfate monohydrate, and any combinations thereof. Non-limiting exemplary derivatives of mineral compounds include salts, alkaline salts, polysaccharides, esters, elemental minerals, and chelates of any mineral compound.

In some embodiments of the invention, the supplemental calcium source in the nutritional composition comprises calcium gluconate alone or in combination with a calcium source selected from the group consisting of calcium lactate, calcium sulfate, calcium chloride, calcium citrate, calcium phosphate, calcium D-saccharate, calcium aspartate, calcium propionate, and combinations thereof. In a particular embodiment of the invention, the sole supplemental calcium source in the nutritional composition comprises calcium gluconate.

In a separate embodiment, the composition of the invention may comprise a children's nutritional composition provided as a growing-up milk. Such invention may have a standard serving size of 200 ml, providing from about 60 to 75 kcal/100 ml of energy, with a recommended intake of two to three servings per day. In such an embodiment, the amounts and types of proteins, lipids and carbohydrates may vary. Protein may comprise from about 2.5 to 3.75 g/100 kcal, with carbohydrate providing from about 11 to about 16.5 g/100 kcal and lipids comprising from about 2.2 to about 4.4 g/100 kcal. Carbohydrate sources may be any known or used in the art as suitable for nutritional compositions, including but not limited to those disclosed herein. In an embodiment, sources of carbohydrate for use in the growing-up milk may include, but are not limited to, maltodextrins, fructose, lactose, prebiotics, resistant starch, starch, and any combinations thereof. In an embodiment, less than 10% of energy per serving of the growing-up milk may be contributed from sugars selected from the group consisting of: white sugar (glucose), brown sugar, corn syrup, corn syrup solids, high fructose corn syrup, malt syrup, maple syrup, liquid fructose, molasses, honey, anhydrous dextrose, and any combinations thereof.

When vitamin A is present in the growing-up milk, it may be present in a range of about 1 to about 150 mcg/serving. In another embodiment, vitamin A may be present in amounts ranging from about 57 to about 65 mcg/serving. Any source of vitamin A known in the art to have nutritional uses, including, but not limited to those previously disclosed for practicing the invention, may be suitable for use in the present composition. In an embodiment, sources of vitamin A for use in the growing-up milk may include preformed sources of vitamin A, such as retinyl acetate, retinyl palmitate, retinol and any combinations thereof.

When Vitamin C is present in the growing-up milk, it may be present in the range of about 0.1 to about 10 mg/serving. In another embodiment, vitamin C may be present at the level of 5 mg/serving. Any source of vitamin C known in the art to have nutritional uses, including, but not limited to those previously disclosed for practicing the invention, may be suitable for use in the present composition. In an embodiment, sources of vitamin C for use in the growing-up milk include L-ascorbic acid, sodium L-ascorbate, calcium L-ascorbate, ascorbyl palmitate, and any combinations thereof.

When thiamin is present in the growing-up milk, it may be present in the range of about 0.01 to about 0.5 mg/serving. In another embodiment, thiamin may be present in the range of 0.05 to about 0.15 mg/serving. In yet another embodiment, thiamin may be in the range of 0.08 to 0.10 mg/serving. Any source of thiamin known in the art to have nutritional uses, including, but not limited to those previously disclosed for practicing the invention, may be suitable for use in the present composition. In an embodiment, sources of thiamin for use in the growing-up milk include thiamin hydrochloride, thiamin mononitrate and any combinations thereof.

When riboflavin is present in the growing-up milk, it may be present in the range of about 0.01 to about 0.5 mg/serving. In another embodiment, riboflavin may be present in the range of 0.05 to about 0.15 mg/serving. In yet another embodiment, riboflavin may be in the range of 0.08 to 0.10 mg/serving. Any source of riboflavin known in the art to have nutritional uses, including, but not limited to those previously disclosed for practicing the invention, may be suitable for use in the present composition. In an embodiment, sources of riboflavin for use in the growing-up milk include free riboflavin, sodium riboflavin, riboflavin-5'phosphate, and any combinations thereof.

When vitamin $B_6$ is present in the growing-up milk, it may be present in the range of about 0.01 to about 0.5 mg/serving. In another embodiment, vitamin $B_6$ may be present in the range of 0.05 to about 0.15 mg/serving. In yet another embodiment, the level of vitamin $B_6$ may be in the range of 0.08 to 0.10 mg/serving. Any source of vitamin $B_6$ known in the art to have nutritional uses, including, but not limited to those previously disclosed for practicing the invention, may be suitable for use in the present composition. In an embodiment, sources of vitamin $B_6$ for use in the growing-up milk include pyridoxine hydrochloride, pyridoxine-5'-phosphate and any combinations thereof.

When folate is present in the growing-up milk, it may be present in the range of 5 to 50 mcg/serving. In another embodiment, the folate content may be 10 to 40 mcg/serving. In yet another embodiment, the folate content may be within the range of 20 to 35 mcg/serving. Any source of folate known in the art to have nutritional uses, including, but not limited to those previously disclosed for practicing the invention, may be suitable for use in the present composition. In an embodiment, the source of folate for use in the growing-up milk is folic acid.

When vitamin D is present in the growing-up milk, it may be present in the range of 0.1 to about 2 mcg/serving. In yet another embodiment, the vitamin D content of the growing-up milk may be 0.5 to 1 mcg/serving. Any source of vitamin D known in the art to have nutritional uses, including, but not limited to those previously disclosed for practicing the present invention, may be suitable for use in the present composition. In an embodiment, sources of vitamin D for use in the growing-up milk include cholecalciferol, ergocalciferol and any combinations thereof.

When calcium is present in the growing-up milk, total calcium may be present in the range of about 165 to about 300 mg/serving. In another embodiment, the level of total calcium in the growing-up milk may be provided in the range of about 180 to 250 mg/serving. Any source of calcium known in the art to have nutritional uses, including, but not limited to those previously disclosed for practicing the present invention, may be suitable for use in the present composition.

When iron is provided in the growing-up milk, it may be present in the range of 0.1 to 2.2 mg/serving. In another embodiment, iron may be present in the range of 0.5 to 1.8 mg/serving. In yet another embodiment, the level of iron provided in the growing-up milk may be in the range of 1.0 to 1.4 mg/serving. Any source of iron known in the art to have nutritional uses, including, but not limited to those previously disclosed for practicing the present invention, may be suitable for use in the present composition. In an embodiment, sources of iron for use in the growing-up milk include ferrous sulfate, ferrous fumarate, and any combinations thereof.

When zinc is provided in the growing-up milk, it may be present in the range of 0.2 to 1.5 mg/serving. In another embodiment, zinc may be present in the range of 0.5 to 1.0 mg/serving. Any source of zinc known in the art to have nutritional uses, including, but not limited to those previously disclosed for practicing the present invention, may be suitable for use in the present composition. In an embodiment, zinc is provided as zinc sulfate.

When iodine is present in the growing-up milk, it may be present in the range of 0.2 to 41 mcg/serving. In another embodiment, iodine may be present in the range of 5 to 15 mcg/serving. Any source of iodine known in the art to have nutritional uses, including, but not limited to those previously disclosed for practicing the present invention, may be suitable for use in the present composition. In an embodiment, sources of iodine for use with the growing-up milk include sodium iodide, potassium iodide and any combinations thereof.

In another embodiment wherein the inventive composition is a growing-up milk formulated for children between the ages of 1 to 6 years, vitamins and minerals may be added in varying amounts and ranges based on a per-serving basis. In an embodiment, one serving of the growing-up milk may contain from about 15% to about 50% of the Estimated Average Requirement (EAR) for children between the ages of 1 and 6 years for the following nutrients: vitamin E, vitamin K, niacin, pantothenic acid, vitamin $B_{12}$, biotin, choline, potassium, magnesium, phosphorus, chloride, copper, selenium, fluoride, and any combinations thereof. In an embodiment, one serving of the growing-up milk may contain from about 20% to about 30% of the EAR for children between the ages of 1 and 6 years for the following nutrients: vitamin E, vitamin K, niacin, pantothenic acid, vitamin $B_{12}$, biotin, choline, potassium, magnesium, phosphorus, chloride, copper, selenium, fluoride, and any combinations thereof. Any known sources of these nutrients having nutritional uses, including, but not limited to those disclosed herein may be suitable for use in the composition.

The composition of the invention may optionally contain other substances that may have a beneficial effect on the host such as lactoferrin, nucleotides, nucleosides, immunoglobulins, CMP equivalents (cytidine 5'-monophosphate, free acid), UMP equivalents (uridine 5'-monophosphate, disodium salt), AMP equivalents (adenosine 5'-monophosphate, free acid), GMP equivalents (guanosine 5'-monophosphate, disodium salt), and combinations thereof.

In one embodiment of the invention, the nutritional composition may contain one or more probiotics. The term "probiotic" means a microorganism that exerts beneficial effects on the health of the host. Any probiotic known in the art may be acceptable in this embodiment provided it achieves the intended result. In a particular embodiment, the probiotic may be selected from *Lactobacillus* species, *Lactobacillus rhamnosus* GG, *Bifidobacterium* species, *Bifidobacterium longum*, and *Bifidobacterium animalis* subsp. *lactis* BB-12.

If included in the composition, the amount of the probiotic may vary from about $10^4$ to about $10^{10}$ colony forming units (cfu) per kg body weight per day. In another embodiment, the amount of the probiotic may vary from about $10^6$ to about $10^9$ cfu per kg body weight per day. In yet another embodiment, the amount of the probiotic may be at least about $10^6$ cfu per kg body weight per day.

In an embodiment, the probiotic(s) may be viable or non-viable. As used herein, the term "viable", refers to live microorganisms. The term "non-viable" or "non-viable probiotic" means non-living probiotic microorganisms, their cellular components and metabolites thereof. Such non-viable probiotics may have been heat-killed or otherwise inactivated but retain the ability to favorably influence the health of the host. The probiotics useful in the present invention may be naturally-occurring, synthetic or developed through the genetic manipulation of organisms, whether such new source is now known or later developed.

In another embodiment of the invention, the nutritional composition may contain one or more prebiotics. The term "prebiotic" as used herein refers to indigestible food ingredients which exert health benefits upon the host. Such health benefits may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Any prebiotic known in the art will be acceptable in this embodiment provided it achieves the desired result. Such prebiotics may be naturally-occurring, synthetic, or developed through the genetic manipulation of organisms and/or plants, whether such new source is now known or developed later. Prebiotics useful in the present invention may include oligosaccharides, polysaccharides, and other prebiotics that contain fructose, xylose, soya, galactose, glucose and mannose. More specifically, prebiotics useful in the present invention may include lactulose, lactosucrose, raffinose, gluco-oligosaccharide, inulin, polydextrose, polydextrose powder, galacto-oligosaccharide, galacto-oligosaccharide syrup, fructo-oligosaccharide, isomalto-oligosaccharide, soybean oligosaccharides, lactosucrose, xylo-oligosacchairde, chito-oligosaccharide, manno-oligosaccharide, aribino-oligosaccharide, siallyl-oligosaccharide, fuco-oligosaccharide, and gentio-oligosaccharides.

In an embodiment, the total amount of prebiotics present in the nutritional composition may be from about 1.0 g/L to about 10.0 g/L of the composition. In another embodiment, the total amount of prebiotics present in the nutritional composition may be from about 2.0 g/L and about 8.0 g/L of the composition. In yet another embodiment, the total amount of prebiotics present in the nutritional composition may be about 4.0 g/L of the composition.

If galacto-oligosaccharide is used as a prebiotic, the amount of galacto-oligosaccharide in the nutritional composition may, in an embodiment, be within the range of from about 1.0 g/L to about 4.0 g/L. In another embodiment, the amount of galacto-oligosaccharide in the nutritional composition may be about 2.0 g/L. In yet another embodiment, the amount of galacto-oligosaccharide in the nutritional composition may be about 4.0 g/L. If polydextrose is used as a prebiotic, the amount of polydextrose in the nutritional composition may, in an embodiment, be within the range of from about 1.0 g/L to about 4.0 g/L. In another embodiment, the amount of polydextrose in the nutritional composition may be about 2.0 g/L. In a particular embodiment, galacto-oligosaccharide and polydextrose are supplemented into the nutritional composition in a total amount of about 4.0 g/L. In this embodiment, the amount of galacto-oligosaccharide may be about 2.0 g/L and the amount of polydextrose may be about 2.0 g/L.

If galacto-oligosaccharide is used as a prebiotic, the amount of galacto-oligosaccharide in the nutritional composition may, in an embodiment, be from about 0.1 mg/100 Kcal to about 1.0 mg/100 Kcal. In another embodiment, the amount of galacto-oligosaccharide in the nutritional composition may be from about 0.1 mg/100 Kcal to about 0.5 mg/100 Kcal. In yet another embodiment, the amount of galacto-oligosaccharide in the nutritional composition may be about 0.6 mg/100 Kcal. If polydextrose is used as a prebiotic, the amount of polydextrose in the nutritional composition may, in an embodiment, be within the range of from about 0.1 mg/100 Kcal to about 0.5 mg/100 Kcal. In another embodiment, the amount of polydextrose may be about 0.3 mg/100 Kcal. In a particular embodiment, galacto-oligosaccharide and polydextrose are supplemented into the nutritional composition in a total amount of about 0.6 mg/100 Kcal. In this embodiment, the amount of galacto-oligosaccharide may be about 0.3 mg/100 Kcal and the amount of polydextrose may be about 0.3 mg/100 Kcal.

In yet another embodiment of the present invention, the formulation may contain other active agents such as long chain polyunsaturated fatty acids (LCPUFAs). Suitable LCPUFAs include, but are not limited to, α-linoleic acid, γ-linoleic acid, linoleic acid, linolenic acid, eicosapentanoic acid (EPA), arachidonic acid (ARA) and/or docosahexaenoic acid (DHA). In an embodiment, the nutritional composition is supplemented with DHA. In another embodiment, the nutritional composition is supplemented with ARA. In yet another embodiment, the nutritional composition is supplemented with both DHA and ARA.

In one embodiment, the nutritional composition is supplemented with both DHA and ARA. In this embodiment, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

In certain embodiments of the invention, the level of DHA is in the range of about 0.0% and 1.00% of fatty acids, by weight. The level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

If included, the amount of DHA in an embodiment of the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

If included, the amount of DHA in the nutritional composition may vary from about 5 mg/100 kcal to about 80 mg/100 kcal. In one embodiment of the present invention, DHA varies from about 10 mg/100 kcal to about 50 mg/100 kcal; and in another embodiment, from about 15 mg/100 kcal to about 20 mg/100 kcal. In a particular embodiment of the present invention, the amount of DHA is about 17 mg/100 kcal.

In embodiments of the invention, the level of ARA is in the range of 0.0% and 0.67% of fatty acids, by weight. In another embodiment, the level of ARA may be about 0.67% by weight. In another embodiment, the level of ARA may be about 0.5% by weight. In yet another embodiment, the level of DHA may be in the range of about 0.47% and 0.48% by weight.

If included, the amount of ARA in an embodiment of the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If included, the amount of ARA in the nutritional composition may vary from about 10 mg/100 kcal to about 100 mg/100 kcal. In one embodiment of the present invention, the amount of ARA varies from about 15 mg/100 kcal to about 70 mg/100 kcal. In another embodiment, the amount of ARA varies from about 20 mg/100 kcal to about 40 mg/100 kcal. In a particular embodiment of the present invention, the amount of ARA is about 25 mg/100 kcal.

If included, the nutritional composition may be supplemented with oils containing DHA and ARA using standard techniques known in the art. For example, DHA and ARA may be added to the formula by replacing an equivalent amount of an oil, such as high oleic sunflower oil, normally present in the formula. As another example, the oils containing DHA and ARA may be added to the formula by replacing an equivalent amount of the rest of the overall fat blend normally present in the formula without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

In one embodiment, a LCPUFA source which contains EPA is used in the nutritional composition. In another embodiment, a LCPUFA source which is substantially free of EPA is used in the nutritional composition. For example, in one embodiment of the present invention, the nutritional composition contains less than about 16 mg EPA/100 kcal. In another embodiment, the nutritional composition contains less than about 10 mg EPA/100 kcal. In yet another embodiment, the nutritional composition contains less than about 5 mg EPA/100 kcal. Another embodiment of the invention includes a nutritional composition that is free of even trace amounts of EPA.

The nutritional composition of the invention also may contain emulsifiers. Examples of suitable emulsifiers include, but are not limited to, lecithin (e.g., from egg or soy), and/or mono- and di-glycerides and mixtures thereof. Other emulsifiers are readily apparent to the skilled artisan and selection of suitable emulsifier(s) will depend, in part, upon the formulation and final product.

The nutritional composition of the invention may optionally contain one or more stabilizers. Suitable stabilizers for use in the nutritional composition of the present invention, include, but are not limited to, gum Arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methylcellulose, hydroxypropyl cellulose, DATEM (diactyl tartaric acid esters of mono- and di-glycerides), dextran, carrageenans, and mixtures thereof.

The nutritional composition of the present invention may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional composition of the present invention may optionally include one or more of the following flavoring agents, including but not limited to, flavored extracts, volatile oils, cocoa or chocolate flavorings, vanilla or vanilla extract, peanut butter flavoring, honey, cookie crumbs or any commercially available flavoring. Further non-limiting examples of flavoring agents useful in the nutritional composition of the present invention include, but are not limited to, pure anise extract, imitation banan extract, imitation cherry extract, chocolate extract, pure lemon extract, pure orange extract, pure peppermint extract, imitation pineapple extract, imitation rum extract, imitation strawberry extract; or volatile oils, such as balm oil, bay oil, bergamot oil, cedarwood oil, cherry oil, cinnamon oil, clove oil, or peppermint oil; butterscotch, toffee, and mixtures thereof. The amounts of flavoring agent can vary greatly depending upon the flavoring agent used. The type and amount of flavoring agent used can be selected as is known in the art.

In a particular embodiment, the composition of the invention is a milk-based nutritional composition which provides physiochemical and physiological benefits. As is known in the art, bovine milk protein comprises two major components: acid soluble whey protein and acid insoluble casein, with the latter representing about 80% of the total protein content of bovine milk. Upon entering the acidic environment of the stomach, casein precipitates and complexes with minerals forming semi-solid curds of varying size and firmness. Softer, smaller curds are easier for the body to digest than larger, harder curds. Curd formation may be an important consideration in the development of nutritional compositions, including, but not limited to infant formulas, medical foods, and premature infant formulas. In an embodiment of the present invention, the composition of the invention provides a nutritional composition having softer and smaller curds than standard infant formulas.

Figure 2:
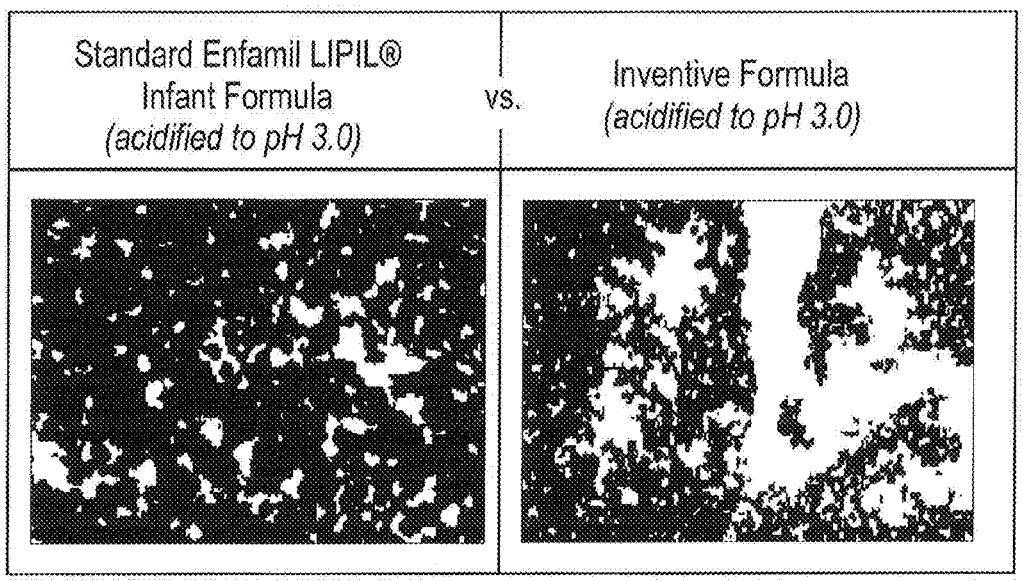
FIG. 2 illustrates a comparison of standard formula versus the inventive formula with regard to curd formation.
Figure 3:
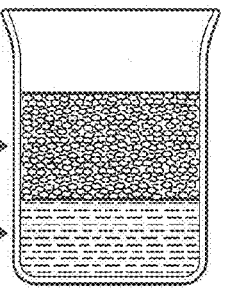
FIG. 3 illustrates a comparison of standard formula versus the inventive formula with regard to curd formation.

For example, FIGS. 1-3 illustrate curd formation in a standard Enfamil LIPIL® infant formula versus the exemplary inventive formula set forth in Example 1. In FIG. 1, shown without acidification, the formulas appear similar. In FIG. 2, however, it can be seen that the inventive formula forms much smaller curds than the standard formula upon acidification, which mimics the acidic environment of the stomach. FIG. 3 illustrates the curd formation of standard infant formula versus the inventive composition at pH 3.5 and 4.0, again mimicking the acidic conditions of the stomach. It can be seen that the curds of the inventive composition have taken on substantially more water than the standard infant formula curds, providing a smaller and softer curd. Accordingly, the inventors have shown that the inventive composition forms much smaller and softer curds than standard formulas.

In addition, the formation of softer and smaller curds provides faster gastric emptying. Thus, in an embodiment, the invention is directed to a method for enhancing the rate of gastric emptying via administration of the composition of the invention. While not wishing to be tied to this or any theory, the inventors believe that enzymatic digestion may be facilitated via the composition of the invention because the digestive enzymes can penetrate the softer and smaller curds more easily than tighter, firmer curds formed in standard formulas. In this embodiment, facilitating faster gastric emptying may reduce the risk of gastroesophageal reflux and aspiration in infants.

The composition of the invention may also provide, in certain embodiments, a finer dispersion of the curds and/or less agglomeration of proteins. The composition may provide improved emulsion properties over standard formulas. Again, not wishing to be bound by this or any theory, it is believed that strong curds are formed having weak water structures. These weak water structures are more easily disrupted and the proteins are more easily denatured, thereby leading to weaker emulsions. The soft curds formed in the composition of the present invention have a strong water structure and are less easily disrupted or denatured and, therefore, exhibit enhanced emulsion properties.

In another embodiment of the invention, the composition provides a greater amount of bioavailable calcium to the consumer. In an embodiment, the composition contains supplemental calcium gluconate, which is more soluble than many calcium salts, which thereby provides a greater amount of bioavailable calcium to the individual consuming the composition.

In yet another embodiment, the composition of the invention provides a prebiotic effect upon conversion to short chain fatty acids in the gut. In this embodiment, the dissociated gluconate from calcium gluconate may provide an enhanced prebiotic effect due to the greater solubility of calcium gluconate.

In certain embodiments, the composition is an infant formula. In this embodiment, the infant formula has characteristics that are more similar than those of standard formula to those of breast milk. The curd formation of the present invention is softer and smaller, which is more similar to those formed from breast milk. In this embodiment, the infant administered the inventive composition will experience softer stool consistency more similar to the breast-fed infant compared with that of standard formula.

In yet another embodiment of the invention, the composition of the invention may contain TGF-β. Transforming growth factor-beta (TGF-β) is the general name for a family of polypeptides, the members of which have multifunctional regulatory activities. Three differentially regulated mammalian isoforms (termed TGF-β1, TGF-β2, and TGF-β3) play important roles in a multitude of processes in the developing embryo, infant, child and adult. TGF-β is a 25-kDa homodimeric cytokine known to mediate pleitropic functions both within the immune system and systemically. TGF-β is expressed in several cell types in the intestinal mucosal including lymphocytes, epithelial cells, macrophages, and stromal cells as well as by T-cells, neutrophils, macrophages, epithelial cells, fibroblasts, platelets, osteoblasts, osteoclasts and others. In addition, TGF-β is present in human breast milk and may influence multiple aspects of infant health and development.

TGF-βs are synthesized as large precursor proteins which consist of an amino-terminal pro-domain, comprising a signal sequence and latency-associated complex, and a mature carboxy-terminal subunit. Biologically active TGF-βs are homodimers which consist of two identical, disulfide-linked mature subunits. Release of the TGF-β homodimer from the latency-associated complex is necessary for TGF-β to exert biological activity on target cells. The nature of the latency-associated complex and the mechanisms responsible for TGF-β release are key to understanding TGF-β biological activity in vivo. In the human gut, this may be accomplished by the action of proteolytic enzymes, pH extremes, heat, calcium, and/or mechanical tearing.

Based on the numerous benefits provided by TGF-β, it is often important that the growth factor is present in, or supplemented into, various nutritional products. For example, certain protein sources in nutritional products may provide a source of TGF-β. Alternatively, if the nutritional product itself does not contain TGF-β, the growth factor may be supplemented into the product. As noted above, however, the release of TGF-β is in its inactive form. The TGF-β present in the protein sources of nutritional products, or added to those nutritional products, is also in its inactive form. It is then activated in the human gut by enzymes, extremes of pH, and/or tearing.

In a particular embodiment, the composition of the invention enhances the bioavailability or bioactivity of TGF-β in the human gut. This may include enhancing the signaling of TGF-β in the human body. In an embodiment, the composition of the invention may enhance the bioactivity of TGF-β in the human gut by at least about 5%. In another embodiment, the composition of the invention may enhance the bioactivity of TGF-β in the human gut by at least about 15%. In yet another embodiment, the composition of the invention may enhance the bioactivity of TGF-β in the human gut by at least about 25%. In a further embodiment, the composition of the invention may enhance the bioactivity of TGF-β in the human gut by at least about 50%. In still another embodiment, the composition of the invention may enhance the bioactivity of TGF-β in the human gut by at least about 66%.

In a further embodiment, the composition of the invention may enhance the bioactivity of TGF-β in the human gut from about 5% to about 15%. In still a further embodiment, the composition of the invention may enhance the bioactivity of TGF-β in the human gut from about 15% to about 50%. In an even further embodiment, the composition of the invention may enhance the bioactivity of TGF-β in the human gut from about 25% to about 75%. In a particular embodiment, the composition of the invention may enhance the bioactivity of TGF-β in the human gut from about 15% to about 65%.

Figure 4:
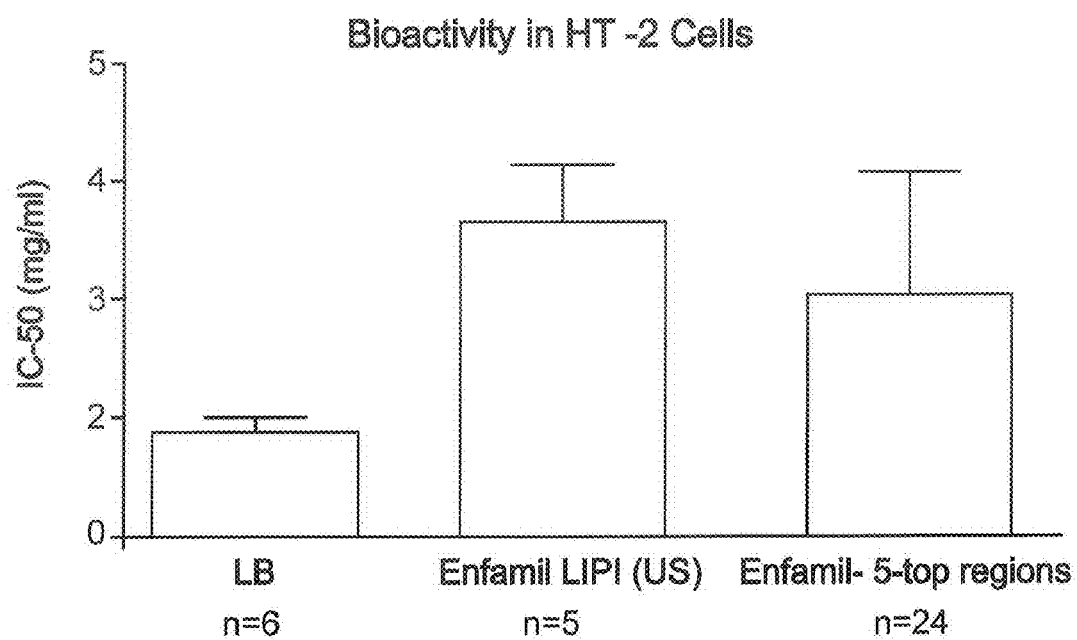
FIG. 4 is a bar chart illustrating the bioactivity of the inventive formula versus the standard formula.

As can be seen in FIG. 4, the bioactivity of TGF-β was measured in a HT-2 cell growth inhibition assay. In this assay, six samples of the present composition were compared to a standard infant formula (Enfamil LIPIL®). Bioactivity was determined as a measure of the $IC_{50}$ value of the composition. The $IC_{50}$ value is a measure of the effectiveness of a composition in inhibiting biological or biochemical function by half. In this case, the $IC_{50}$ value is the concentration at which inhibition of the bioactivity in the HT-2 cells is 50% maximum. Table 1 illustrates the $IC_{50}$ values for the compositions tested.

TABLE 1

IC$_{50}$ Comparisons of Standard and Inventive Formulas

| Sample | IC$_{50}$ Value |
| --- | --- |
| Inventive Composition LEOAd0201FP | 1.7 mg/ml |
| Inventive Composition LEOAd0701FP | 1.8 mg/ml |
| Inventive Composition LEOAd2901FP | 1.3 mg/ml |
| Inventive Composition LEOAa3101FP | 1.3 mg/ml |
| Inventive Composition LEOAa3201FP | 1.4 mg/ml |
| Inventive Composition LEOAa3301FP | 1.3 mg/ml |
| Standard Enfamil ® LIPIL ® Infant Formula (U.S.) | 4.2 mg/ml |
| Standard Enfamil ® Infant Formula (Top 5 Regions) | 3.2 mg/ml |

The average IC$_{50}$±standard deviation for the inventive composition was 1.46 mg/ml±0.2 mg/ml. The average IC$_{50}$ for the standard U.S. formula was 4.2 mg/ml and the average IC$_{50}$ for the standard formula in the top 5 worldwide regions (U.S., Mexico, Thailand, China, and Philippines) was 3.2. Thus, in a comparison of the standard U.S. formula versus the inventive composition, the IC$_{50}$ of the inventive composition was one-third that of the standard U.S. formula. The inventive composition, therefore, enhances the bioactivity of TGF-β. FIG. 4 illustrates these values. The inventive formulation is labeled as "LB."

In a particular embodiment of the invention, the level of TGF-β in the inventive composition is from about 0.0150 (pg/μg) ppm to about 0.1000 (pg/μg) ppm. In another embodiment, the level of TGF-β in the inventive composition is from about 0.0225 (pg/μg) ppm to about 0.0750 (pg/μg) ppm. In yet another embodiment, the level of TGF-β in the inventive composition is from about 0.0300 (pg/μg) ppm to about 0.0600 (pg/μg) ppm. In a particular embodiment, the level of TGF-β in the inventive composition is about 0.0340 (pg/μg) ppm.

In a particular embodiment of the invention, the level of TGF-β in the inventive composition is from about 2500 pg/mL to about 10,000 pg/mL composition. In another embodiment, the level of TGF-β in the inventive composition is from about 3000 pg/mL to about 8000 pg/mL. In yet another embodiment, the level of TGF-β in the inventive composition is from about 4000 pg/mL to about 6000 pg/mL. In a particular embodiment, the level of TGF-β in the inventive composition is about 5000 pg/mL.

In an embodiment, the level of TGF-β1 in the inventive composition is from about 0.0001 (pg/μg) ppm to about 0.0075 (pg/μg) ppm. In another embodiment, the level of TGF-β1 in the inventive composition is from about 0.0010 (pg/μg) ppm to about 0.0050 (pg/μg) ppm. In yet another embodiment, the level of TGF-β1 in the inventive composition is from about 0.0020 (pg/μg) ppm to about 0.0035 (pg/μg) ppm. In still another embodiment, the level of TGF-β1 in the inventive composition is about 0.0030 (pg/μg) ppm.

In an embodiment, the level of TGF-β2 in the inventive composition is from about 0.0150 (pg/μg) ppm to about 0.0750 (pg/μg) ppm. In another embodiment, the level of TGF-β2 in the inventive composition is from about 0.0250 (pg/μg) ppm to about 0.0500 (pg/μg) ppm. In yet another embodiment, the level of TGF-β2 in the inventive composition is from about 0.0300 (pg/μg) ppm to about 0.0400 (pg/μg) ppm. In still another embodiment, the level of TGF-β2 in the inventive composition is about 0.0320 (pg/μg) ppm.

In an embodiment, the ratio of TGF-β1:TGF-β2 in the inventive composition is in the range of about 1:1 to about 1:20. In another embodiment, the ratio of TGF-β1:TGF-β2 in the inventive composition is in the range of about 1:5 to about 1:15. In still another embodiment, the ratio of TGF-β1:TGF-β2 in the inventive composition is in the range of about 1:8 to about 1:13. In a particular embodiment, the ratio of TGF-β1:TGF-β2 in the inventive composition is about 1:11.

In an embodiment, the bioactivity of TGF-β within the inventive composition is from about 500 nanogram equivalents (ng Eq)/100 kcal to about 5000 ng Eq/100 kcal. In another embodiment, the bioactivity of TGF-β within the inventive composition is from about 750 ng Eq/100 kcal to about 3000 ng Eq/100 kcal. In yet another embodiment, the bioactivity of TGF-β within the inventive composition is from about 800 ng Eq/100 kcal to about 2500 ng Eq/100 kcal. In one embodiment, the bioactivity is about 860 ng Eq/100 kcal. In another embodiment, the bioactivity is about 1700 ng Eq/100 kcal. In another embodiment, the bioactivity is about 1200 ng Eq/100 kcal.

Alternatively, the bioactivity of TGF-β in the inventive composition can be defined in terms of IC$_{50}$ in a HT-2 cell growth inhibition assay. In an embodiment, the bioactivity of the composition comprises an IC$_{50}$ from about 1.1 mg/ml to about 5.0 mg/ml. In another embodiment, the bioactivity of the composition comprises an IC$_{50}$ from about 1.2 mg/ml to about 3.0 mg/ml. In yet another embodiment, the bioactivity of the composition comprises an IC$_{50}$ from about 1.3 mg/ml to about 3.0 mg/ml. In still another embodiment, the bioactivity of the composition comprises an IC$_{50}$ from about 1.3 mg/ml to about 2.0 mg/ml. In an embodiment, the bioactivity of the composition comprises an IC$_{50}$ of about 1.5 mg/ml.

In an embodiment of the invention, the TGF-β levels, bioactivities, and ratios are maintained during and after digestion.

While not wishing to be bound by this or any theory, the enhanced TGF-β bioactivity in the human gut may be due to the composition of the invention lowering the pH of the infant gut and allowing a greater or faster activation of TGF-β. In addition to enhancing the activation of TGF-β bioactivity in the human gut, it is believed that the inventive composition may additionally enhance other bioactive components in the human gut. Thus, in an embodiment, the invention is directed to a method for enhancing the bioactivity of one or more bioactive factors in the human gut.

In some embodiments, the bioactivity of TGF-β in a nutritional composition is enhanced by the addition of a bioactive whey fraction. Any bioactive whey fraction known in the art may be used in this embodiment provided it achieves the intended result. In an embodiment, this bioactive whey fraction may be a whey protein concentrate. In a particular embodiment, the whey protein concentrate may be Salibra® 800, available from Glanbia Nutritionals. In a particular embodiment, the Salibra® 800 whey protein concentrate is 2.5% acidified. In another embodiment, the Salibra® 800 whey protein concentrate is 5% acidified. In yet another embodiment, the Salibra® 800 whey protein concentrate is 2% acidified. In a further embodiment, the Salibra® 800 whey protein concentrate is 3% acidified.

The addition of Salibra® 800 whey protein concentrate to the inventive composition may provide a level of TGF-β from about 75 ng/100 kcal to about 300 ng/100 kcal. In another embodiment, the addition of Salibra® 800 whey protein concentrate to the inventive composition may provide a level of TGF-β of from about 100 ng/100 kcal to about 220 ng/100 kcal.

The addition of Salibra® 800 whey protein concentrate to the inventive composition may provide a level of TGF-β from about 0.75 μg/100 kcal to about 1.5 μg/100 kcal. In another embodiment, the addition of Salibra® 800 whey protein concentrate to the inventive composition may provide a level of TGF-β of from about 0.80 μg/100 kcal to about 1.30 μg/100 kcal. The ratio of TGF-β1:TGF-β2 may be from about 1:1 to about 1:10. In an embodiment, the ratio of TGF-β1:TGF-β2 may be about 1:6.

The addition of Salibra® 800 whey protein concentrate to the inventive composition may enhance the bioactivity of TGF-β by about 20 to 40%. In another embodiment, the addition of Salibra® 800 whey protein concentrate to the inventive composition may enhance the bioactivity of TGF-β by at least 20%.

In another embodiment, the whey protein concentrate may be Nutri Whey 800, available from DMV International. In yet another embodiment, the whey protein concentrate may be Salibra-850, available from Glanbia Nutritionals. In still another embodiment, the whey protein concentrate may be Prolacta Lacatalis WPI90, available from Lactilus Industrie U.S.A., Inc. In a further embodiment, the whey protein concentrate may be supplied by MG Nutritionals.

In some embodiments, the composition of the invention induces oral tolerance. As used herein, the term "oral tolerance" refers to the specific suppression of cellular and/or humoral immune responses to an antigen by prior administration of the antigen by the oral route. Oral tolerance affects the responsiveness of the local immune system in the intestinal mucosa itself, thus preventing hypersensitivity reactions to food proteins that could otherwise elicit potent inflammatory reactions in the gut. Development of oral tolerance is an important component in appropriate mucosal immune function. Oral antigens, like food or commensal bacteria, are normally processed in a manner that results in a regulated immune response. This response does not injure the host and results in systemic hypo-responsiveness in subsequent oral challenge with the same food antigen. Thus oral tolerance is established. Oral tolerance can fail, however, in response to the development and pathogenesis of several immunologically based diseases, including inflammatory bowel disease, Crohn's disease, and ulcerative colitis. In a particular embodiment, the combination of TGF-β and the prebiotics of the present invention may synergistically contribute to the induction of oral tolerance to antigens in circumstances where oral tolerance has previously failed. In some embodiments, the induction of oral tolerance may be enhanced by administration of the composition of the invention. In other embodiments, the oral tolerance acquired by a subject may be maintained by administration of the composition of the invention.

In certain embodiments, the invention is also directed to a method for enhancing the mucosal immune response in an infant or child comprising administration of the nutritional composition of the present invention. In some embodiments, the enhancement of the mucosal immune response may include promoting maturation and differentiation of intestinal epithelial cells and/or improved nutrient absorption. In some embodiments, the enhancement of the mucosal immune response may include stimulation of intestinal barrier integrity and/or reducing intestinal permeability. In this embodiment, the enhancement of mucosal immune response may facilitate a properly functioning intestinal mucosal barrier which is able to distinguish between and allow the passage of potentially beneficial substances while actively serving as a barrier against those that may be hazardous so that they do not reach the systemic circulation. In some embodiments, the enhancement of the mucosal immune response may include improvement of mucin synthesis, secretion, and/or quality and/or increasing the production of soluble anti-microbial factors.

In certain embodiments, the invention is also directed to a method for supporting favorable T helper cell-mediated responses in an infant or child comprising the administration of the nutritional composition of the present invention. In some embodiments, a favorable T helper cell-mediated response may include an attenuated Th2 response in response to exposure to environmental allergens. In this embodiment, an attenuated Th2 response characterized by less induction of interleukins IL-4, IL-13, and IL-5 by Th2 cells, subsequent attenuation of IgE production by B-cells, eosinophil activation and recruitment, and mucus production may act in concert to lessen the risk of chronic allergic conditions including, but not limited to, allergic inflammation, allergic rhinitis, atopic dermatitis, allergic asthma, hay fever, and any combinations thereof. In some embodiments, a favorable T helper cell-mediated response may include more aggressive Th1 interferon-gamma (IFN-γ) secretion. In a separate embodiment, a favorable T helper cell-mediated response refers to a balanced Th1-Th2 response following exposure to environmental antigens such that there is polarization towards neither a Th1 nor a Th2 profile and a balanced immune response is achieved. In this embodiment, Th1-Th2 balance may lessen the risk of chronic allergic conditions including, but not limited to, allergic inflammation, allergic rhinitis, atopic dermatitis, allergic asthma, hay fever, and any combinations thereof.

In embodiments, the invention may be directed to the use of the inventive composition for softening the stool of a subject. The invention may also be directed to the inventive composition for use in softening the stool of a subject.

The invention may be directed to the use of the inventive composition for increasing the rate of gastric emptying in a subject. The invention may also be directed to the inventive composition for use in increasing the rate of gastric emptying in a subject.

The invention may be directed to the use of the inventive composition for producing a short-chain fatty acid profile in a formula-fed infant that is similar to that produced in a breast-fed infant. The invention may also be directed to the inventive composition for use in producing a short-chain fatty acid profile in a formula-fed infant that is similar to that produced in a breast-fed infant.

There are differences in the bacterial species in the gut of the breast-fed and formula-fed infant. In the breast-fed infant, for example, with the beneficial *Bifidobacterium* spp. being dominate among intestinal bacterial. The intestinal microflora is more diverse in the formula-fed infant, with *Bifidobacteria* spp. present but significantly more pathogenic species, including *Staphylococcus, Escherichia coli* and *Clostridia*, than is found in the breast-fed infant. In an embodiment, the invention may be directed to the use of the inventive composition for increasing the population and species of beneficial bacteria and decreasing the population and species of pathogenic bacteria in the intestine of an infant fed the infant formula.

In addition, the intestinal short chain fatty acid (SCFA) profile of the breast-fed infant is very different from that of the formula-fed infant. Breast-fed infants produce virtually no butyrate, with acetate comprising greater than 95% of total SCFA production. While acetate (74%) is also the major SCFA in feces of formula-fed infants, there is also a considerable amount of propionate that is produced (23%). In an embodiment, the invention may be directed to the use of the inventive composition towards a SCFA profile that is more similar to the breast-fed infant. In this embodiment, the shift in SCFA profile by the administration of the inventive composition may promote a gut microflora profile more similar to the breast-fed infant thereby reducing the risk of pathogenic infections, promoting gastrointestinal development, improving nutrient absorption, and reducing discomfort caused by excessive gas production from intestinal bacteria discomfort in the formula-fed infant.

The invention may be directed to the use of the inventive composition for preventing or reducing systemic inflammation in a subject by reducing the release of one or more pro-inflammatory cytokines or chemokines. As used herein, "pro-inflammatory" cytokines or chemokines include those known in the art to be involved in the up-regulation of inflammatory reactions. Examples include, but are not limited to, TNF-α, IL-1β, IL-6, IL-8, IL-18, and GRO-KC.

In certain embodiments, the invention is also directed to a method for enhancing immunity and/or suppressing inflammation in a pediatric subject comprising the administration of the composition of the invention. In some embodiments, the enhancement of immunity or suppression of inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T- and B-cell immunity; stimulation of a helper T-cell 1 (Th1) cytokine pattern (increased interleukin-1 (IL-1), IL-2, interferon-gamma (IFN-γ), IL-12, tumor necrosis factor-alpha (TNF-α); human leukocyte antigen-Dr (HLA-Dr) expression); suppression of inflammation or production of systemic and mucosal inflammatory mediators (including cytokines and/or chemokines); reduction of sensitization by reducing total and/or allergen-specific immunoglobulin E (IgE); reduction of the production of allergic cytokines; reduction of a Th2 supporting immunoglobulin profile; and combinations thereof.

In some embodiments, the prevention or reduction of inflammation is systemic. The term "systemic", as used herein, means relating to or affecting the entire body. This type of inflammation may include localized inflammation at specific sites, but may also be associated with general "flu-like" symptoms, including fever, chills, fatigue or loss of energy, headaches, loss of appetite, and muscle stiffness.

In another embodiment, the invention is directed to methods for treating or preventing respiratory syncytial virus (RSV), RSV-induced inflammation, airway hyperresponsiveness, colitis, and/or endotoxemia via administration of the composition of the invention. Example 4 illustrates the effectiveness of the composition in treating or preventing the above conditions.

The invention may be directed to the use of the inventive composition for preventing or reducing a condition selected from the group consisting of respiratory syncytial virus, respiratory syncytial virus-induced inflammation, airway hyper-responsiveness, colitis, and endotoxemia. The invention may also be directed to the inventive composition for use in preventing or reducing a condition selected from the group consisting of respiratory syncytial virus, respiratory syncytial virus-induced inflammation, airway hyperresponsiveness, colitis, and endotoxemia.

In some embodiments of the present invention, the subject to be treated is in need of the particular treatment, reduction, or prevention. The subject may be at risk due to genetic predisposition, diet, lifestyle, diseases, disorders, and the like. For example, a preterm infant or immunosuppressed subject may be at risk for systemic inflammation and may, therefore, be in need of such treatment, reduction, or prevention.

In the methods of the invention, the subject may, in some embodiments, be an infant. The methods of the invention may be applied to an infant, young child, neonate, pediatric subject, or child. If the method is applied to a "neonate", such term may be defined as a human that is less than about 1 month old. As used herein, the term "child" or "children" shall encompass humans between the age of about 3 years and prior to adolescence. The term "pediatric", as used herein, may encompass infants, young children, children, and adolescents.

In a certain embodiment, the invention comprises a means for communicating information about the benefits of the nutritional composition of claim 1 or benefits of the use of calcium gluconate as the supplemental calcium source in a nutritional composition comprising: the formation of softer curds upon acidification in the human gut; the formation of smaller curds upon acidification in the human gut; the improvement of digestibility; the softening of the stool; the increase of the rate of gastric emptying; the enhancing of bioavailability of calcium; the production of a short-chain fatty acid profile in a formula-fed infant that is similar to that produced in a breast-fed infant; the increasing of the population and species of beneficial bacteria in the gut of a formula-fed infant; the reduction of systemic inflammation in a subject; the treatment of a condition selected from the group consisting of respiratory syncytial virus infection, respiratory syncytial virus-induced inflammation, airway hyperresponsiveness, colitis, and endotoxemia; or the enhancing of the bioactivity of TGF-β, comprising a document, digital storage media, optical storage media, audio presentation, or visual display containing the information or instruction. In some embodiments, the communication means is a displayed web site, a brochure, a product label, a package insert, an advertisement, or a visual display.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example illustrates an embodiment of a powdered infant formula of the present invention.

TABLE 2

| Ingredients | |
|---|---|
| Ingredient | Amount per 100 kg |
| Lactose, Grind A | 35.119 kg |
| Palm Olein Oil | 12.264 kg |
| Coconut Oil | 5.451 kg |
| Soy Oil | 5.451 kg |
| High Oleic Sunflower Oil | 4.088 kg |
| Non-Fat Dry Milk, Medium-Heat, Spray Dried | 14.667 kg |

TABLE 2-continued

Ingredients

| Ingredient | Amount per 100 kg |
|---|---|
| Whey Protein Concentrate, 35% Protein, Super Sack | 14.667 kg |
| Galacto-Oligosaccharide Syrup (77% solids, 44% fiber) | 3.477 kg |
| Polydextrose Power (96% total solids, 96% carbohydrate, 86% fiber) | 1.770 kg |
| Calcium Gluconate, Monohydrate | 1.606 kg |
| Single Cell Arachidonic Acid Oil | 0.347 kg |
| Single Cell Docosahexaenoic Acid Oil | 0.238 kg |
| Choline Bitartrate | 0.228 kg |
| Potassium Chloride | 0.198 kg |
| Sodium Chloride | 24.780 g |
| Magnesium Oxide, Light | 22.790 g |
| L-Carnitine | 9.910 g |
| Ascorbic Acid | 156.687 g |
| Inositol | 39.887 g |
| Corn Syrup Solids | 35.478 g |
| Taurine | 33.875 g |
| Dry vitamin E Tocopheryl Acetate, 50% | 25.279 g |
| Vitamin A Palmitate, Dry Beadlets, CW Dispersible, 250 | 7.871 g |
| Niacinamide | 6.475 g |
| Vitamin K1 Dry Phytonadione USP Powder, 1% | 5.454 g |
| Calcium Pantothenate | 3.299 g |
| Vitamin $B_{12}$, 0.1% in starch | 2.122 g |
| Biotin Trituration, 1% | 1.608 g |
| Vitamin $D_3$ Powder | 0.969 g |
| Riboflavin | 0.755 g |
| Thiamine Hydrochloride | 0.601 g |
| Pyridoxine Hydrochloride | 0.518 g |
| Folic Acid | 0.122 g |
| Corn Syrup Solids | 192.187 g |
| Ferrous Sulfate, Heptahydrate | 49.600 g |
| Ascorbic Acid | 6.213 g |
| Malto-Dextrin | 146.096 g |
| Cytidine 5'-Monohphosphate, Free Acid | 11.604 g |
| Uridine 5'-Monophosphate, Disodium Salt | 3.419 g |
| Adenosine 5'-Monophosphate, Free Acid | 2.711 g |
| Guanosine 5'-Monophosphate, Disodium Salt | 2.170 g |
| Lactose, Grind A | 138.017 g |
| Zinc Sulfate, Monohydrate | 16.422 g |
| Corn Syrup Solids | 3.616 g |
| Sodium Selenite, Anhydrous | 0.018 g |
| Cupric Sulfate, Powder ($CuSO_4 \cdot 5H_2O$) | 1.688 g |
| Manganese Sulfate, Monohydrate | 0.239 g |

TABLE 3

Proximate Analysis

| | Grams per 100 g | Grams per 100 mL at Normal Dilution | Caloric Distribution |
|---|---|---|---|
| Protein | 10.84 | 1.47 | 8.50 |
| Fat | 28.57 | 3.89 | 50.67 |
| Carbohydrate | 54.87 | 7.46 | 40.83 |
| Ash | 2.70 | 0.37 | |
| Moisture | 3.02 | 89.9 | |
| Calories | 508 | 69.1 | |

TABLE 4

Nutrients

| Nutrient | Quantities per 100 Calories |
|---|---|
| Calories | 100 |
| Protein, g | 2.1 |
| Fat, g | 5.6 |
| Carbohydrates, g | 10.6 |
| Ash, g | 0.6 |
| Water, mL (normal dilution) | 133 |
| Linoleic Acid, mg | 900 |
| α-Linolenic Acid, mg | 85 |
| Arachidonic Acid, mg | 25 |
| Docosahexaenoic Acid, mg | 17 |
| Vitamin A, IU | 300 |
| Vitamin D, IU | 60 |
| Vitamin E, IU | 2 |
| Vitamin K, mcg | 8 |
| Thiamin, mcg | 80 |
| Riboflavin, mcg | 140 |
| Vitamin $B_6$, mcg | 60 |
| Vitamin $B_{12}$, mcg | 0.3 |
| Niacin, mcg | 1000 |
| Folic Acid, mcg | 16 |
| Pantothenic Acid, mcg | 500 |
| Biotin, mcg | 3 |
| Vitamin C, mg | 12 |
| Choline, mg | 24 |
| Inositol, mg | 6 |
| Taurine, mg | 6 |
| Carnitine, mg | 2 |
| Calcium, mg | 78 |
| Phosphorus, mg | 43 |
| Magnesium, mg | 8 |
| Iron, mg | 1.8 |
| Zinc, mg | 1 |
| Manganese, mcg | 15 |
| Copper, mcg | 75 |
| Iodine, mcg | 10 |
| Sodium, mg | 27 |
| Potassium, mg | 108 |
| Chloride, mg | 63 |
| Selenium, mcg | 2.8 |
| Polydextrose | 0.3 |
| Galacto-oligosaccharide | 0.3 |
| AMP Equivalents, mg | 0.5 |
| CMP Equivalents, mg | 2.5 |
| GMP Equivalents, mg | 0.3 |
| UMP Equivalents, mg | 0.9 |
| Nucleotide Equivalents, mg | 4.2 |

To prepare 1 liter of product at standard dilution (20 kcal/fl. oz.), 136 grams of powder was mixed with 895.2 grams of water. To prepare 1 quart of product at standard dilution, 128.7 grams of powder was mixed with 847.2 grams water.

Upon reconstitution, the infant formula described in this example contains approximately 2 g/L of galacto-oligosaccharide and 2 g/L of polydextrose. The infant formula has an ARA level of 25 mg/100 kcal. The formula contains 5.6 g fat/100 kcal, to achieve a fat content which is similar to human milk. The formula additionally has a low buffer strength.

All pH adjustments with regard to this infant formula were made with solutions of potassium hydroxide. The specific gravity of the formula is 1.03117.

EXAMPLE 2

This example illustrates another embodiment of a powdered infant formula of the present invention.

TABLE 5

Ingredients

| Ingredient | Amount per 100 kg |
|---|---|
| Lactose, Grind A | 34.277 kg |
| Palm Olein Oil | 12.267 kg |

TABLE 5-continued

Ingredients

| Ingredient | Amount per 100 kg |
|---|---|
| Coconut Oil | 5.452 kg |
| Soy Oil | 5.452 kg |
| High Oleic Sunflower Oil | 4.089 kg |
| Non-Fat Dry Milk, Medium-Heat, Spray Dried | 14.670 kg |
| Whey Protein Concentrate, 35% Protein, Super Sack | 14.670 kg |
| Galacto-Oligosaccharide Syrup (77% solids, 44% fiber) | 6.840 kg |
| Calcium Gluconate, Monohydrate | 1.606 kg |
| Single Cell Arachidonic Acid Oil | 0.347 kg |
| Single Cell Docosahexaenoic Acid Oil | 0.238 kg |
| Choline Bitartrate | 0.228 kg |
| Potassium Chloride | 0.198 kg |
| Sodium Chloride | 24.780 g |
| Magnesium Oxide, Light | 22.794 g |
| L-Carnitine | 9.911 g |
| Ascorbic Acid | 146.436 g |
| Inositol | 37.278 g |
| Corn Syrup Solids | 33.159 g |
| Taurine | 31.659 g |
| Dry vitamin E Tocopheryl Acetate, 50% | 23.625 g |
| Vitamin A Palmitate, Dry Beadlets, CW Dispersible, 250 | 7.356 g |
| Niacinamide | 6.051 g |
| Vitamin K1 Dry Phytonadione USP Powder, 1% | 5.097 g |
| Calcium Pantothenate | 3.084 g |
| Vitamin $B_{12}$, 0.1% in starch | 1.983 g |
| Biotin Trituration, 1% | 1.503 g |
| Vitamin $D_3$ Powder | 0.906 g |
| Riboflavin | 0.705 g |
| Thiamine Hydrochloride | 0.561 g |
| Pyridoxine Hydrochloride | 0.483 g |
| Folic Acid | 0.114 g |
| Corn Syrup Solids | 192.187 g |
| Ferrous Sulfate, Heptahydrate | 49.600 g |
| Ascorbic Acid | 6.213 g |
| Malto-Dextrin | 146.096 g |
| Cytidine 5'-Monophosphate, Free Acid | 11.604 g |
| Uridine 5'-Monophosphate, Disodium Salt | 3.419 g |
| Adenosine 5'-Monophosphate, Free Acid | 2.711 g |
| Guanosine 5'-Monophosphate, Disodium Salt | 2.170 g |
| Lactose, Grind A | 138.017 g |
| Zinc Sulfate, Monohydrate | 16.422 g |
| Corn Syrup Solids | 3.616 g |
| Sodium Selenite, Anhydrous | 0.018 g |
| Cupric Sulfate, Powder ($CuSO_4 \cdot 5H_2O$) | 1.688 g |
| Manganese Sulfate, Monohydrate | 0.239 g |

TABLE 6

Proximate Analysis

| | Grams per 100 g | Grams per 100 mL at Normal Dilution | Caloric Distribution |
|---|---|---|---|
| Protein | 10.84 | 1.47 | 8.34 |
| Fat | 28.57 | 3.89 | 49.50 |
| Carbohydrate | 54.87 | 7.46 | 42.16 |
| Ash | 2.70 | 0.37 | |
| Moisture | 3.02 | 89.9 | |
| Calories | 510 | 69.4 | |

TABLE 7

Nutrients

| Nutrient | Quantities per 100 Calories |
|---|---|
| Calories | 100 |
| Protein, g | 2.1 |
| Fat, g | 5.6 |
| Carbohydrates, g | 10.6 |
| Ash, g | 0.6 |
| Water, mL (normal dilution) | 133 |
| Linoleic Acid, mg | 900 |
| α-Linolenic Acid, mg | 85 |
| Arachidonic Acid, mg | 25 |
| Docosahexaenoic Acid, mg | 17 |
| Vitamin A, IU | 300 |
| Vitamin D, IU | 60 |
| Vitamin E, IU | 2 |
| Vitamin K, mcg | 8 |
| Thiamin, mcg | 80 |
| Riboflavin, mcg | 140 |
| Vitamin $B_6$, mcg | 60 |
| Vitamin $B_{12}$, mcg | 0.3 |
| Niacin, mcg | 1000 |
| Folic Acid, mcg | 16 |
| Pantothenic Acid, mcg | 500 |
| Biotin, mcg | 3 |
| Vitamin C, mg | 12 |
| Choline, mg | 24 |
| Inositol, mg | 6 |
| Taurine, mg | 6 |
| Carnitine, mg | 2 |
| Calcium, mg | 78 |
| Phosphorus, mg | 43 |
| Magnesium, mg | 8 |
| Iron, mg | 1.8 |
| Zinc, mg | 1 |
| Manganese, mcg | 15 |
| Copper, mcg | 75 |
| Iodine, mcg | 10 |
| Sodium, mg | 27 |
| Potassium, mg | 108 |
| Chloride, mg | 63 |
| Selenium, mcg | 2.8 |
| Galacto-oligosaccharide | 0.6 |
| AMP Equivalents, mg | 0.5 |
| CMP Equivalents, mg | 2.5 |
| GMP Equivalents, mg | 0.3 |
| UMP Equivalents, mg | 0.9 |
| Nucleotide Equivalents, mg | 4.2 |

To prepare 1 liter of product at standard dilution (20 kcal/fl. oz.), 136 grams of powder was mixed with 895.2 grams of water. To prepare 1 quart of product at standard dilution, 128.7 grams of powder was mixed with 847.2 grams water.

Upon reconstitution, the infant formula described in this example contains approximately 4 g/L of galacto-oligosaccharide and has an ARA level of 25 mg/100 kcal. The formula contains 5.6 g fat/100 kcal, to achieve a fat content which is similar to human milk. The formula additionally has a low buffer strength.

All pH adjustments with regard to this infant formula were made with solutions of potassium hydroxide. The specific gravity of the formula is 1.03117.

EXAMPLE 3

This example compares the indicators of calcium status in neonatal pigs fed completely nutritionally adequate diets that differ in the source of calcium and the presence of oligosaccharides in a 2×2 factorial design.

All diets will be provided by Mead Johnson and formulated based on the nutritional requirements of neonatal pigs. This basal diet (BD=Enfamil® LIPIL® infant formula that meets piglet nutrient requirement) will also contain long-chain polyunsaturated fatty acids (LCPUFAs) at a level to be specified by Mead Johnson. All diets will contain identical concentrations of calcium, though differing sources, which will meet or slightly exceed the requirement of neonatal pigs. Two of the diets will contain the oligosaccharides polydextrose (PDX) and galacto-oligosaccharide (GOS). The diets are set forth below.

Diet 1) BD+Calcium Carbonate
Diet 2) BD+Calcium Gluconate
Diet 3) Diet 1+2 g/L PDX+2 g/L GOS
Diet 4) Diet 2+2 g/L PDX+2 g/L GOS Protocol: A total of 70 pigs (24-36 hours old) of similar body weight will be utilized in two replicates of this study (35 pigs per replicate). For each replicate, 7 piglets will be euthanized prior to the start of the study to provide base line data on bone mineral content. The remaining 28 pigs will be housed individually and assigned to one of the four dietary treatments for 15 days. Individual body weights will be recorded daily and plasma collected initially and at day 5, 10 and 15 of this study. All plasma samples will be analyzed for the hormonal form of vitamin D ($1,25(OH)_2D_3$) concentration and parathyroid hormone (PTH) concentration by ELISA. These plasma hormones are the best physiological indicators of increased calcium absorption when the animals are at or above their dietary calcium requirements. If there were to be an increase in passive or non-vitamin D mediated calcium uptake, both PTH and $1,25(OH)_2D_3$ concentrations would drop dramatically and calcium excretion into the urine would increase. By looking at these hormones and the urinary calcium levels we are obtaining a complete picture of the calcium status of the animals. This is needed when comparing different calcium sources under nutritionally calcium adequate conditions, because by definition dietary calcium levels above requirement should not increase bone mineral accretion. Additionally, plasma levels of calcium, phosphorus, total alkaline phosphatase activity and bone specific alkaline phosphatase activity will be determined in these samples. These values will be normalized using total plasma protein in order to account for variations in plasma volume due to hydration state. Additionally, after each blood collection, urine will be also be collected by cytocentesis. Calcium concentrations in the urine will be determined and normalized to creatine. These plasma and urinary measures will give us a complete picture of the calcium status of these pigs at multiple time points during the feeding trial.

At the completion of the study, all animals will be euthanized and the left radial bone and the left tenth rib collected for bone mineral content analysis by ashing. The right radial bones will also be collected and utilized in 3 point bending tests to determine the load applied and displacement at yield and from these values the modulus will be calculated. Samples will also be collected from the duodenum, ileum and colon for histology, the quantification of lactobacillus species, and for short chain fatty acid analysis. These data will help to validate the results of a previous trial conducted with dietary oligosaccharide supplementation by Dr. Odle's group. Additionally, digesta samples from the stomach, small intestine, and colon will be collected and snap frozen for shipment to Mead Johnson.

In Support of Calcium Bioequivalency:
Plasma Analysis (Initial, Day 5, Day 10, and Day 15):
$1,25(OH)_2D_3$
PTH
Inorganic Phosphorus
Calcium
Total alkaline phosphatase activity
Bone specific alkaline phosphatase
Bone Integrity Analysis in support of Calcium Bioequivalency:
Calcium concentrations in the urine will be determined and normalized to creatine.
Urine Analysis in support of Calcium Bioequivalency:
Flexural testing (3 point bending)
Fresh bone weight and dimensions
Bone Ash Percentage
In Support of EW1B Non-Clinicals:
Plasma Analysis (Day 15):
Plasma Fatty Acid profile (Day 15)
Blood phenotype (hemoglobin, hematocrit, WBC, RBC, Platelets, Neutrophils & Lymphocytes)
Save plasma from all collection dates for MJN usage (measure TGF-β levels and bioactivity)
Intestinal:
Histology on sections of duodenum, ileum, and colon
Stomach, ileal, cecal and colonic pH
Quantification of *Lactobacillus* (duodenum, ileum, and colon)
Short Chain Fatty Acid (duodenum, ileum, and colon)
Collection of digesta samples from stomach, duodenum, ileum, and colon for MJN usage (measure TGF-β levels and bioactivity, protein digestion)

EXAMPLE 4

This example illustrates the effect of the inventive composition on RSV-induced lung inflammation and airway hyperresponsiveness and remodeling.

Four to six week old mice will administered the composition of the invention for 2 days prior to and 3 days following RSV infection. At the end of treatment, animals will be infected with RSV and we will investigate the effect of administration of the composition on RSV-induced clinical disease (illness score, body weight loss and airway hyperesponsiveness), pulmonary inflammation, mucin production and changes in airway thickness. We will also investigate Smad 2 and 3 activation to determine the effect of the composition in the lungs of uninfected and infected mice. Mice will be sacrificed at defined time post-infection (p.i.) to determine the effect of diet administration on:

Lung inflammation by measuring total and differential cell counts (day 1, 3, 7, 14, 21 and 28 p.i.)
Cytokine and chemokine production by Bio-Plex, including TGFbeta.
Viral replication by plaque assay (day 5, peak of viral titer)
Airway hyperesponsiveness (day 1 to day 28 p.i.)
Mucin staining and morphometric analysis for airway thickness (day 5, 14, 21 and 28 p.i.)
Smad 2/3 activation (day 0, 0.5, 1, 3 and 5 p.i.)

At the end of treatment, mice will be inoculated intranasally (i.n.) with $1 \times 10^7$ plaque forming units (PFU) of RSV diluted in phosphate buffered saline (PBS) under light anesthesia. Control mice will be inoculated with the same volume of either PBS or supernatant from uninfected Hep-2 cells processed in the same way as infected cells used for the preparation of purified RSV (referred as sham infection). At the indicated time points after infection, mice will be euthanized with an intraperitoneal injection of ketamine and xylazine.

We will perform the majority of the animal studies described using n=5 animals per group for each experimental condition. If two groups will be compared, mean values will be compared by t-test and paired t-test (or nonparametric equivalent). If more than two groups, mean values will be compared by ANOVA (or nonparametric equivalent).

Clinical Illness and Viral Replication.

BALB/c mice infected with RSV show a progressive loss of body weight during the first three days of infection, which usually recovers by day seven of infection, and ruffled fur 10. For studies of "clinical illness" mice will be infected with RSV, in the presence or absence of PUFA, and assessed daily, up to seven days, by two observers using a well-established grading scale (1 to 5) (0=healthy, 1=barely ruffled fur, 2=ruffled fur but active, 3=ruffled fur and inactive, 4=ruffled fur, inactive and hunched, 5=Dead) (10). Daily determination of body weight will also be used to monitor progression of the disease. We will determine viral titers in lung tissue by plaque assay on day 5 p.i., which represents the peak day of viral titer.

Airway Obstruction and Hyperresponsiveness (AHR).

Whole-body plethysmography (Buxco Electronics, Inc. Sharon, Conn.) will be utilized to monitor the respiratory dynamics, specifically, Enhanced Pause (Penh) (see below), in RSV-infected mice in a quantitative manner with and without methacholine challenge. A major advantage of this technique is that it allows multiple determinations of pulmonary function over time in individual animals. The instrument is located in the Division of Clinical and Experimental Immunology and Infectious Diseases, and is available to the members of the Division, as well to other investigators of the Department of Pediatrics of UTMB.

Airway Obstruction

Penh is a dimensionless value that represents a function of the ratio of peak expiratory flow to peak inspiratory flow and a function of the timing of expiration. Penh correlates with pulmonary airflow resistance or obstruction. Penh as measured by plethysmography has been previously validated in animal models of AHR and models of infection-associated airway obstruction. For the determination of airway obstruction, baseline Penh will be recorded daily in groups of sham-inoculated or RSV-infected, unrestrained BALB/c mice. We will focus particularly on the early phase of infection (days 1-5), during the resolution phase (days 7-10), and during the "convalescence phase" (up to four weeks after infection).

AHR

In these studies, we will examine AHR following methacholine challenge. AHR will be determined at different time points of RSV infection, although the main interest will be at the "convalescence phase" when we expect that the acute effect of infection on pulmonary pathology/function may have subsided. Prior to methacholine exposure, mice will be allowed to acclimate to the vented exposure chamber and plethysmograph readings recorded to establish baseline values. Mice will then receive nebulized doses of methacholine (via a Pari IS-2 nebulizer). Immediately after each methacholine exposure Penh readings will be taken and averaged for three minutes. A total of five methacholine doses (3, 6, 12, 24, and 48 mg/ml) will be administered. Groups of RSV-infected and sham-inoculated control mice will be evaluated in parallel at all time points during the entire study.

Pulmonary Inflammation.

Anesthetized and tracheotomized mice will be cannulated with a 1 ml syringe and the lungs flushed three times, with 1 mL of sterile cold PBS. Total cellular influx and differential cell counts will be measured in the BAL of all experimental groups. Total cell counts will be determined by staining 50 μl of BAL with trypan blue and counting viable cells using a hemocytometer. For differentials, 100 μl of BAL will be used to generate cytospin preparations. Slides will be dried fixed and stained with Protocol Hema3 (Fisher Diagnostics, Middletown, Va.). A total number of 300 cells will be counted per sample using light microscopy.

Mucin Production and Morphometric Airway Analysis.

Lungs will be perfused, removed, and fixed in 10% buffered formalin and embedded in paraffin. Multiple 4 μm longitudinal cross-sections will be stained with either Periodic-acid Schiff (PAS) or with haematoxylin & eosin (H&E). The slides will be analyzed and scored for mucin content and airway wall thickness by a board certified pathologist.

Western Blot Assay for Smad Activation.

Total cell lysates from uninfected and infected mice will be fractionated by SDS-PAGE, and transferred to polyvinylidene difluoride membranes. Membranes will be blocked with 5% milk in TBS-Tween and incubated with anti-phospho Smad 2/3 antibody, recognizing the Ser465 and Ser467 phosphorylated form of both Smad 2 and 3 (Cell Signaling). Proper horseradish-coupled secondary antibody will be used and proteins detected by enhanced chemiluminescence assay (Amersham, Piscataway, N.J.). Membranes will be stripped and reprobed with regular anti-Smad 2 and 3 antibody, to verify equal loading of the samples.

EXAMPLE 5

This example illustrates a comparison of calcium carbonate and calcium gluconate in infant formula diets meeting calcium requirements of neonatal pigs both with and without oligosaccharide supplementation. In this study, the feeding of calcium carbonate was compared to the feeding of calcium gluconate in diets with and without oligosaccharide supplementation.

Twenty-eight neonatal pigs from aged from 1 to 15 days were used in the example. The formula was provided in equal amounts to the pigs 3 times daily via a gravity-fed nipple feeding system at a rate designed to allow growth similar to that of sow-raised piglets. Diets were formulated to be nutritionally equivalent and to contain 1.3% calcium, which was intended to slightly exceed the nutritional requirements of the pigs.

A significant effect of calcium source ($P<0.01$) on growth performance was seen. Pigs receiving formulas containing calcium carbonate had higher rates of body weight gain, feed intake, and efficiency of body weight gain than those receiving calcium gluconate. Thus, calcium gluconate may have a weight-management effect by modulating body weight gain and feed intake.

While initially there were no significant differences in plasma calcium or phosphorous concentrations among any of the treatment groups, at day 5 and day 10 of feeding, pigs fed the calcium gluconate formulas had higher ($P<0.01$) plasma calcium concentrations and lower ($P<0.01$) plasma inorganic phosphorous concentrations. However, by the end of the study, there was no longer a significant difference in plasma calcium concentrations based on dietary calcium source but plasma inorganic phosphorous was still significantly lower ($P<0.01$) in pigs fed the calcium gluconate-containing formulas.

At the completion of the study there were no significant effects of calcium source on the length, fresh weight, dry weight, or ash weight of the radial and ulna bones of the pigs. The maximum load tolerated by these bones during 3-point flexural testing was, however, significantly greater ($P<0.05$) in calcium gluconate-fed pigs. Additionally, there was a trend for higher bone ash % ($P<0.06$) in the calcium gluconate-fed pigs.

While not wishing to be tied to this or any theory, the inventors believe that these results suggest that mineral homeostasis in the neonatal animal may be less tightly regulated and, therefore, the relative bioavailability of calcium sources is of much greater importance in neonatal diets than in those of older animals.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. An infant formula comprising:
   a. a protein source comprising about 1.8 to about 2.5 g/100 Kcal;
   b. a fat source comprising about 5.5 to about 5.7 g/100 Kcal;
   c. a carbohydrate source comprising about 10.5 to about 11.0 g/100 Kcal;
   d. a supplemental calcium source comprising calcium gluconate, calcium D-saccharate, calcium aspartate, calcium propionate, and combinations thereof;
   e. DHA comprising about 15 to about 20 mg/100 Kcal;
   f. ARA comprising about 23 to about 27 mg/100 Kcal;
   g. a prebiotic comprising:
      i. about 0.5 to about 0.7 mg/100 Kcal galacto-oligosaccharide; or
      ii. about 0.2 to about 0.4 mg/100 Kcal polydextrose and about 0.2 to about 0.4 mg/100 Kcal galacto-oligosaccharide; and
   h. TGF-$\beta$.

2. The infant formula of claim 1 wherein from about 40% to about 70% of protein source comprises whey protein.

3. The infant formula of claim 1 wherein from about 30% to about 60% of protein source comprises casein.

4. The infant formula of claim 1 wherein calcium gluconate is the sole supplemental calcium source.

5. The infant formula of claim 1 wherein the product is a composition selected from the group consisting of infant formula, children's nutritional product, pediatric nutritional formula, toddler nutritional formula, growing up milk, human milk supplement, and medical food.

6. The infant formula of claim 1 wherein the product is in a form selected from the group consisting of powder, liquid concentrate, ready-to-use, and acidified product.

7. The infant formula of claim 1 wherein the product is added to human milk prior to consumption.

8. The infant formula of claim 1 wherein the prebiotic comprises about 0.5 to about 0.7 mg/100 Kcal galacto-oligosaccharide.

9. The infant formula of claim 1 wherein the prebiotic comprises about 0.2 to about 0.4 mg/100 Kcal polydextrose and about 0.2 to about 0.4 mg/100 Kcal galacto-oligosaccharide.

10. The infant formula of claim 1 wherein the fat source comprises about 5.6 g/100 Kcal.

11. The infant formula of claim 1 wherein DHA comprises about 17 mg/100 Kcal.

12. The infant formula of claim 1 wherein ARA comprises about 25 mg/100 Kcal.

13. The infant formula of claim 1 wherein TGF-$\beta$ is present in a level of from about 0.0150 (pg/$\mu$g) ppm to about 0.1000 (pg/$\mu$g) ppm.

14. The infant formula of claim 1 wherein TGF-$\beta$ is present in a level of from about 0.0300 (pg/$\mu$g) ppm to about 0.0600 (pg/$\mu$g) ppm.

15. The infant formula of claim 1 wherein TGF-$\beta$ is present in a level of from about 2500 pg/mL to about 10,000 pg/mL.

16. The infant formula of claim 1 wherein TGF-$\beta$ is present in a level of from about 4000 pg/mL to about 6000 pg/mL.

17. The infant formula of claim 1 wherein the TGF-$\beta$ has a bioactivity of from about 500 ng Eq/100 kcal to about 5000 ng Eq/100 kcal.

18. The infant formula of claim 1 wherein the TGF-$\beta$ has a bioactivity of from about 800 ng Eq/100 kcal to about 2500 ng Eq/100 kcal.

19. The infant formula of claim 1 wherein the TGF-$\beta$ comprises TGF-$\beta$1 and TGF-$\beta$2 and the ratio of TGF-$\beta$1:TGF-$\beta$2 is from about 1:5 to about 1:15.

20. The infant formula of claim 1 wherein the TGF-$\beta$ comprises TGF-$\beta$1 and TGF-$\beta$2 and the ratio of TGF-$\beta$1:TGF-$\beta$2 is from about 1:8 to about 1:13.

21. The infant formula of claim 1 additionally comprising an added source of TGF-$\beta$.

22. The infant formula of claim 21 wherein the additional source of TGF-$\beta$ comprises a whey protein concentrate.

23. The infant formula of claim 1 wherein the supplemental calcium source further comprises calcium lactate, calcium sulfate, calcium chloride, calcium citrate, calcium phosphate and combinations thereof.

* * * * *